(12) United States Patent
Yu et al.

(10) Patent No.: US 12,335,652 B2
(45) Date of Patent: Jun. 17, 2025

(54) MEDICAL SPECTROSCOPY AND IMAGING ANALYSIS

(71) Applicant: Genetic Innovations, Inc., Honolulu, HI (US)

(72) Inventors: Jeffrey N. Yu, Honolulu, HI (US); Lalit K. Mestha, Cohoes, NY (US); Sohail A. Dianat, Pittsford, NY (US)

(73) Assignee: Genetic Innovations, Inc., Honolulu, HI (US)

( * ) Notice: Subject to any disclaimer, the term of this patent is extended or adjusted under 35 U.S.C. 154(b) by 294 days.

(21) Appl. No.: 18/168,263

(22) Filed: Feb. 13, 2023

(65) Prior Publication Data

US 2024/0031514 A1    Jan. 25, 2024

Related U.S. Application Data

(60) Provisional application No. 63/269,526, filed on Mar. 17, 2022, provisional application No. 63/269,525,
(Continued)

(51) Int. Cl.
*G06T 7/32* (2017.01)
*G01N 21/27* (2006.01)
(Continued)

(52) U.S. Cl.
CPC ........... *H04N 5/2628* (2013.01); *G01N 21/27* (2013.01); *G06T 5/70* (2024.01); *G06T 7/32* (2017.01); *G06T 7/90* (2017.01); *G06T 11/00* (2013.01); *H04N 23/85* (2023.01); *G01N 2021/1748* (2013.01); *G01N 2021/1776* (2013.01); *G06T 2207/10024* (2013.01); *G06T 2207/20021* (2013.01); *G06T 2207/20081* (2013.01); *G06T 2207/30004* (2013.01); *G06T 2210/41* (2013.01)

(58) Field of Classification Search
CPC .... G06N 3/045; G06N 3/0464; G06N 3/0475; G06N 3/084; G01N 2021/1765; G01N 1/30; G16H 50/20; G16H 30/40
See application file for complete search history.

(56) References Cited

U.S. PATENT DOCUMENTS 11,482,320 B2 * 10/2022 Klaiman ............... G06T 7/0012
2021/0304401 A1 * 9/2021 Lau ....................... G06T 7/0012
(Continued)

FOREIGN PATENT DOCUMENTS

CN        109906051 A  *  6/2019  ......... A61B 5/04001
WO    WO-2019160580 A1  *  8/2019  ............... G01N 1/30

OTHER PUBLICATIONS

Signoroni A, Savardi M, Baronio A, Benini S. Deep learning meets hyperspectral image analysis: A multidisciplinary review. Journal of imaging. May 8, 2019.*

*Primary Examiner* — Fabio S Lima
(74) *Attorney, Agent, or Firm* — Perkins Coie LLP

(57) ABSTRACT

Systems and methods for medical imaging and spectroscopy analysis are disclosed. Some embodiments relate to digital staining. Some embodiments relate to digital staining using hyperspectral or multispectral imaging. Some embodiments relate to digital staining using RGB imaging. Some embodiments relate to analysis of other types of medical imaging and spectroscopy. Some embodiments relate to platform for performing analysis of medical imaging and spectroscopy data.

20 Claims, 21 Drawing Sheets

Related U.S. Application Data filed on Mar. 17, 2022, provisional application No. 63/315,889, filed on Mar. 2, 2022, provisional application No. 63/310,014, filed on Feb. 14, 2022.

(51) Int. Cl.
  *G06T 5/70*    (2024.01)
  *G06T 7/90*    (2017.01)
  *G06T 11/00*   (2006.01)
  *H04N 5/262*   (2006.01)
  *H04N 23/85*   (2023.01)
  *G01N 21/17*   (2006.01)

(56) References Cited

U.S. PATENT DOCUMENTS

2024/0029409 A1* 1/2024 Aidt .................. G06V 10/22
2024/0290473 A1* 8/2024 Ozcan ................ A61B 5/4331

* cited by examiner

MEDICAL SPECTROSCOPY AND IMAGING ANALYSIS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

This application claims the benefit of U.S. Provisional Application No. 63/310,014, entitled "HYPERSPECTRAL IMAGING ANALYSIS PLATFORM," filed Feb. 14, 2022, U.S. Provisional Application No. 63/315,889, entitled "REAL TIME DIGITAL STAINING OF HYPERSPECTRAL IMAGES," filed Mar. 2, 2022, U.S. Provisional Application No. 63/269,526, entitled "ABSORPTION-BASED SPECTRAL MATCHING FOR DIGITAL STAINING," filed Mar. 17, 2022, and U.S. Provisional Application No. 63/269,525, entitled "MULTIPLEXED DIGITAL STAINING WITH SPECTRAL MATCHING," filed Mar. 17, 2022, the contents of which are incorporated herein in their entirety.

BACKGROUND

Field

Embodiments relate to the field of medical imaging and, in particular, to methods, systems, and devices for analyzing and visualizing complex imaging data. Some embodiments relate to digital staining.

Background

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section.

Chemical staining of tissue samples is a time-intensive, laborious process. A typical formalin-fixed, paraffin-embedded sample may take more than a day to prepare. Frozen tissue samples can be prepared more quickly but may still take considerable time to prepare. Moreover, chemical staining processes are generally destructive. That is, once a sample is stained, it is generally not possible to apply a different stain. For example, tissue samples are commonly stained using hematoxylin and eosin (H&E). In many cases, a pathologist or researcher may wish to identify and/or differentiate components that were observed in H&E-stained tissue samples. However, applying a different stain may necessitate preparing a new tissue slide.

Chemical staining processes are destructive. Once a stain is applied, it is generally not possible to remove the stain and apply another in its place. In many cases, a pathologist or researcher may wish to differentiate and/or identify components observed in tissue sections that were previously stained. For example, a sample may be stained using hematoxylin and eosin initially, and a pathologist may then wish to apply a different stain, for example to detect microorganisms, lipids, carbohydrates, minerals, pigments, and so forth in the tissue sample. Using traditional chemical staining, this can necessitate the preparation of new tissue samples.

Moreover, it can be difficult to analyze stained tissues and other types of medical imaging data, such as CT scans, x-rays, MRI scans, PET scans, and so forth. Often, practitioners may struggle to interpret images and may fail to recognize significant image features that are relevant to treatment or diagnosis.

In some cases, practitioners may lack the resources or knowledge to deploy advanced medical imaging and spectroscopy analysis themselves.

SUMMARY

Digital staining can alleviate many issues found in physical staining. Using digital staining, less preparation time may be needed, and the need to prepare multiple tissue samples whenever additional staining is desired may be reduced or eliminated. Digital staining may, for example, collect a hyperspectral image and then apply one or more transformations to the hyperspectral image to produce one or more digitally stained images. In some cases, an entire hyperspectral image may be captured before digital staining is performed.

In some cases, it may be desirable for a pathologist or other individual to observe staining in real time or near real time. For example, if a pathologist can see a digitally stained image as a tissue sample is being scanned, the pathologist may be able to change course (for example, if the digitally stained image does not appear useful for some reason), develop additional strategies (for example, determine additional staining to apply), and so forth without having to wait for the entire imaging and digital staining process to complete. In some embodiments, a pathologist may select a different region in the tissue sample to enable rapid turnaround time and scanning throughput since unstained tissue sample does not provide enough contrast to make such decisions.

In some cases, a platform that enables medical imaging and spectroscopy analysis may be desirable.

In some aspects, the techniques described herein relate to a computer-implemented method for identifying a feature of interest in a raw image, the computer-implemented method including: accessing, by a computing system, raw image data; determining, by the computing system, a feature of interest in the raw image data; outputting, by the computing system, an indication of a location of the feature of interest in the raw image data; generating, by the computing system, an output voxel for each voxel in the raw image data, each output voxel in the visible spectrum; outputting, by the computing system, an image based on the generated output voxels; and wherein the computing system includes a computer processor and an electronic storage medium.

In some aspects, the techniques described herein relate to a computer-implemented method, wherein the raw image data includes a hyperspectral image.

In some aspects, the techniques described herein relate to a computer-implemented method, wherein generating an output voxels for each voxels in the raw image data includes applying a transformation matrix to the each voxel in the raw image data.

In some aspects, the techniques described herein relate to a remote computing system for image analysis, the computing system including: one or more hardware computer processors; a network communications interface; one or more computer data stores; and computer-executable instructions stored in the one or more computer data stores, wherein the computer-executable instructions, when retrieved from the one or more computer data stores and executed by the one or more computer processors cause the remote computing system to: receive, through the network communications interface, a raw image; receive, through the network communications interface, a request to apply a transformation; generate a transformed image, wherein generating the transformed image includes performing the transformation on the raw image; transmit, through the network communications interface, the transformed image to a user computer system.

In some aspects, the techniques described herein relate to a remote computing system, further including computer-executable instructions stored in the one or more data stores, wherein the computer-executable instructions, when retrieved from the one or more data stores and executed by the one or more processors, cause the remote computing system to: identify one or more features of interest in the raw image; and recommend, based at least in part on the one or more identified features of interest, one or more additional processing steps to apply to the raw image.

In some aspects, the techniques described herein relate to a remote computing system, further including computer-executable instructions stored in the one or more data stores, wherein the computer-executable instructions, when retrieved from the one or more data stores and executed by the one or more processors, cause the remote computing system to: automatically perform the one or more recommended additional processing steps to the raw image;

In some aspects, the techniques described herein relate to a remote computing system, further including computer-executable instructions stored in the one or more data stores, wherein the computer-executable instructions, when retrieved from the one or more data stores and executed by the one or more processors, cause the remote computing system to: automatically identify, based on raw image, one or more features present in the raw image.

In some aspects, the techniques described herein relate to a remote computing system, further including computer-executable instructions stored in the one or more data stores, wherein the computer-executable instructions, when retrieved from the one or more data stores and executed by the one or more processors, cause the remote computing system to: transmit, to the user computer system, an indication of one or more locations of the one or more automatically identified features present in the raw image.

In some aspects, the techniques described herein relate to an image analysis system including: a raw image data store; a plurality of image transformation matrices; an artificial intelligence model; and an application programming interface configured to allow third-party developers to interact with the image analysis system, wherein the image analysis system is configured to be run a computer system.

In some aspects, the techniques described herein relate to an image analysis system, further including a payment system, wherein the payment system is configured to collect payments from users of the image analysis system and to make payments to third-party developers.

In some aspects, the techniques described herein relate to a computer system for generating a model for electronically generating a digitally stained medical image of a tissue sample, the computer system including: a camera; one or more processors; and an electronic storage medium, the camera configured to receive first visible light through an aperture of the camera; the camera configured to generate a first image including red, green, and blue channels from the received first visible light, wherein the first image is a first RGB image of an unstained tissue sample; the camera configured to receive second visible light through the aperture of the camera; the camera configured to generate a second image including red, green, and blue channels from the received second visible light, wherein the second image is a second RGB image of a stained tissue sample, wherein the unstained tissue sample and the stained tissue include a same tissue; the camera is in electronic communication with the one or more processors and the electronic storage medium; the camera configured to electronically store the first and second images in the electronic storage medium; the electronic storage medium includes instructions that, when executed by the one or more processors, cause the one or more processors to: execute first registration instructions including: determining a first difference between the first image and the second image; modifying one or more of the first image and the second image, wherein the modifying includes one or more of rotation, translation, or deformation; determining a second difference between first image and the second image; determining that the second difference between the first image and second image is within an acceptable threshold value; and generating a co-registered image pair including an unstained image and a ground truth image, wherein the unstained image includes the first image or the modified first image and the ground truth image includes the second image or the modified second image; execute a first model training process including: digitally staining the unstained image to generate a first digitally stained image; and computing a loss function, wherein the loss function considers a subset of ground truth image data and a subset of digitally stained image data considers the differences between individual pixels of the ground truth image and the first digitally stained image and differences in a spatial distribution of colors in the ground truth image and the first digitally stained image; and based at least in part on a result of the loss function, adjusting one or more weights of the model; determining that an output of the loss function is within a threshold amount; execute second registration instructions including: determining a third difference between the first digitally stained image generated by the trained model and the ground truth image; modifying one or more of the unstained image and the ground truth image, wherein the modifying includes one or more of rotation, translation, or deformation; determining a fourth difference between the first digitally stained image and the ground truth image; determining that the fourth difference is less within another acceptable threshold value; and generating a second co-registered image pair including a second ground truth image including the ground truth image or the modified ground truth image and a second unstained image including the unstained image or the modified unstained image; execute a second model training process including: digitally staining the second unstained image to generate a second digitally stained image; computing a second loss function, wherein the second loss function considers a subset of second ground truth image data and a subset of second digitally stained image data; and based on a result of the second loss function, adjusting one or more weights of the model; and store a generated digital staining model generated by the first model training process and the second model training process in the electronic storage medium, wherein the generated digital staining model includes the one or more weights.

In some aspects, the techniques described herein relate to a system, wherein the camera includes a Bayer filter and one of a charge-coupled device sensor or a complementary metal oxide semiconductor sensor.

In some aspects, the techniques described herein relate to a system, wherein the first registration instructions further include: denoising at least one of the first image or the second image.

In some aspects, the techniques described herein relate to a system, wherein a difference between a first structural similarity index for the co-registered image pair and a second structural similarity index measure for the second co-registered image pair is about eight percent.

In some aspects, the techniques described herein relate to a system, wherein a registration error between the unstained image and the ground truth image is less than about 10 pixels, wherein the registration error is a measure of an offset between the unstained image and the ground truth image.

In some aspects, the techniques described herein relate to a system, wherein digitally staining the unstained image includes: dividing the unstained image into a first plurality of subfields, each subfield of the first plurality of subfields representing a subset of the unstained image; dividing the stained image into a second plurality of subfields, each subfield of the second plurality of subfields representing a subset of the stained image, wherein each subfield of the second plurality of subfields corresponds to a subfield of the first plurality of subfields; digitally staining each subfield of the second plurality of subfields; and combining each digitally stained subfield to form the digitally stained image.

In some aspects, the techniques described herein relate to a system, wherein at least one subfield of the plurality overlaps with another field of the plurality of subfields.

In some aspects, the techniques described herein relate to a system, wherein a size of a subfield is at least 256 pixels by 256 pixels.

In some aspects, the techniques described herein relate to a system, wherein the size of a subfield is 512 pixels by 512 pixels.

In some aspects, the techniques described herein relate to a method for generating a model for electronically generating a digitally stained medical image of a tissue sample, the method including: receiving a first image including red, green, and blue channels, wherein the first image is an image of an unstained tissue sample, wherein the first image was captured using a camera; receiving a second image including red, green, and blue channels, wherein the second image is an image of a stained tissue sample, wherein the second image was captured using the camera, wherein the unstained tissue sample and the stained tissue include a same tissue; execute first registration instructions including: determining a first difference between the first image and the second image; modifying one or more of the first image and the second image, wherein the modifying includes one or more of rotation, translation, or deformation; determining a second difference between first image and the second image; determining that the second difference between the first image and second image is within an acceptable threshold value; and generating a co-registered image pair including an unstained image and a ground truth image, wherein the unstained image includes the first image or the modified first image and the ground truth image includes the second image or the modified second image; execute a first model training process including: digitally staining the unstained image to generate a first digitally stained image; and computing a loss function, wherein the loss function considers a subset of ground truth image data and a subset of digitally stained image data considers the differences between individual pixels of the ground truth image and the first digitally stained image and differences in a spatial distribution of colors in the ground truth image and the first digitally stained image; and based at least in part on a result of the loss function, adjusting one or more weights of the model; determining that an output of the loss function is within a threshold amount; execute second registration instructions including: determining a third difference between the a digitally stained image generated by the trained model and the ground truth image; modifying one or more of the unstained image and the ground truth image, wherein the modifying includes one or more of rotation, translation, or deformation; determining a fourth difference between the first digitally stained image and the ground truth image; determining that the fourth difference is less within another acceptable threshold value; and generating a second co-registered image pair including a second ground truth image including the ground truth image or the modified ground truth image and a second unstained image including the unstained image or the modified unstained image; execute a second model training process including: digitally staining the second unstained image to generate a second digitally stained image; computing a second loss function, wherein the second loss function considers a subset of second ground truth image data and a subset of second digitally stained image data; and based on a result of the second loss function, adjusting one or more weights of the model; and store a generated digital staining model generated by the first model training process and the second model training process in an electronic storage medium, wherein the generated digital staining model includes the one or more weights.

In some aspects, the techniques described herein relate to a method, wherein the method is repeated using a second tissue sample from a second donor that is different from a first donor of the tissue sample.

In some aspects, the techniques described herein relate to a method, wherein a registration error between the unstained image and the ground truth image is less than about 10 pixels, wherein the registration error is a measure of an offset between the unstained image and the ground truth image.

In some aspects, the techniques described herein relate to a method, wherein the first registration instructions further include: denoising at least one of the first image or the second image.

In some aspects, the techniques described herein relate to a method, wherein a registration error between the first image and the second image is less than about 10 pixels, wherein the registration error is a measure of an offset between the first image and second image.

In some aspects, the techniques described herein relate to a method, wherein digitally staining the unstained image includes: dividing the unstained image into a first plurality of subfields, each subfield of the first plurality of subfields representing a subset of the unstained image; diving the stained image into a second plurality of subfields, each subfield of the second plurality of subfields representing a subset of the stained image, wherein each subfield of the second plurality of subfields corresponds to a subfield of the first plurality of subfields; digitally staining each subfield of the second plurality of subfields; and combining each digitally stained subfield to form the digitally stained image.

In some aspects, the techniques described herein relate to a method, wherein at least one subfield of the plurality overlaps with another field of the plurality of subfields.

In some aspects, the techniques described herein relate to a method, wherein a size of a subfield is at least 256 pixels by 256 pixels.

In some aspects, the techniques described herein relate to a method, wherein the size of a subfield is 512 pixels by 512 pixels.

In some aspects, the techniques described herein relate to a system for electronically generating a digitally stained medical image 9; generate, by the generated model using the preprocessed image, a digitally stained image; and normalize colors of the digitally stained image.

In some aspects, the techniques described herein relate to a system, wherein normalizing the colors of the digitally stained images includes: converting a reference image to a first YCbCr image, wherein the first YCbCr image includes a luma component (Y), a blue-difference chroma component (Cb), and a red-difference chroma component (Cr); determining a mean value for each of the luma component, the blue-difference chroma component, and the red-difference chroma component of the first YCbCr image; determining a standard deviation value for each of the luma component, the blue-difference chroma component, and the red-difference chroma component of the first YCbCr image; converting to digitally stained image to a second YCbCr image, wherein the second YCbCr image includes a luma component (Y), a blue-difference chroma component (Cb), and a read-difference chroma component (Cr); determining a mean value for each of the luma component, the blue-difference chroma component, and the red-difference chroma component of the second YCbCr image; determining a standard deviation value for each of the luma component, the blue-difference chroma component, and the red-difference chroma component of the second YCbCr image; for each pixel of the second YCbCr image, determining a standard deviation of the luma component, the blue-difference chroma component, and the red-difference chroma component; for each pixel in the second YCbCr image: determining a difference between the luma component value of the pixel and the mean value of the luma component for the second YCbCr image; modifying the value of the luma component of the pixel based on the determined difference, the mean luma value of the first YCbCr image, and the standard deviation of the luma value of the first YCbCr image; determining a difference between the blue-difference chroma component value of the pixel and the mean value of the blue-difference chroma component of the second YCbCr image; modifying the value of the blue-difference chroma component of the pixel based on the determined difference, the mean blue difference chroma component value of the first YCbCr image, and the standard deviation of the blue difference chroma component value of the first YCbCr image; determining a difference between the red-difference component value of the pixel and the mean value of the red-difference chroma component of the second YCbCr image; modifying the value of the red-difference chroma component of the pixel based on the determined difference, the mean red-difference chroma component value of the first YCbCr image, and the standard deviation of the red-difference chroma component value of the first YCbCr image; converting the modified values to red, green, and blue values; and generating an RGB image using the red, green, and blue values.

In some aspects, the techniques described herein relate to a system, wherein the reference image is a stained image.

In some aspects, the techniques described herein relate to a system, wherein the reference image is an image of a same tissue type as the tissue sample.

In some aspects, the techniques described herein relate to a system, wherein preprocessing the unstained image includes one or more of resizing, compressing, changing a color space, denoising, or downsampling.

In some aspects, the techniques described herein relate to a method for electronically generating a digitally stained medical image 9; generating, by the generated model using the preprocessed image, a digitally stained image; and normalizing colors of the digitally stained image.

In some aspects, the techniques described herein relate to a method, wherein normalizing the colors of the digitally stained images includes: converting a reference image to a first YCbCr image, wherein the first YCbCr image includes a luma component (Y), a blue-difference chroma component (Cb), and a red-difference chroma component (Cr); determining a mean value for each of the luma component, the blue-difference chroma component, and the red-difference chroma component of the first YCbCr image; determining a standard deviation value for each of the luma component, the blue-difference chroma component, and the red-difference chroma component of the first YCbCr image; converting to digitally stained image to a second YCbCr image, wherein the second YCbCr image includes a luma component (Y), a blue-difference chroma component (Cb), and a read-difference chroma component (Cr); determining a mean value for each of the luma component, the blue-difference chroma component, and the red-difference chroma component of the second YCbCr image; determining a standard deviation value for each of the luma component, the blue-difference chroma component, and the red-difference chroma component of the second YCbCr image; for each pixel of the second YCbCr image, determining a standard deviation of the luma component, the blue-difference chroma component, and the red-difference chroma component; for each pixel in the second YCbCr image: determining a difference between the luma component value of the pixel and the mean value of the luma component for the second YCbCr image; modifying the value of the luma component of the pixel based on the determined difference, the mean luma value of the first YCbCr image, and the standard deviation of the luma value of the first YCbCr image; determining a difference between the blue-difference chroma component value of the pixel and the mean value of the blue-difference chroma component of the second YCbCr image; modifying the value of the blue-difference chroma component of the pixel based on the determined difference, the mean blue difference chroma component value of the first YCbCr image, and the standard deviation of the blue difference chroma component value of the first YCbCr image; determining a difference between the red-difference component value of the pixel and the mean value of the red-difference chroma component of the second YCbCr image; modifying the value of the red-difference chroma component of the pixel based on the determined difference, the mean red-difference chroma component value of the first YCbCr image, and the standard deviation of the red-difference chroma component value of the first YCbCr image; converting the modified values to red, green, and blue values; and generating an RGB image using the red, green, and blue values.

In some aspects, the techniques described herein relate to a method, wherein the reference image is a stained image.

In some aspects, the techniques described herein relate to a method, wherein the reference image is an image of a same tissue type as the tissue sample.

In some aspects, the techniques described herein relate to a method, wherein preprocessing the unstained image includes one or more of resizing, compressing, changing a color space, denoising, or downsampling.

In some aspects, the techniques described herein relate to a computer system for generating a model for electronically generating a digitally stained medical image of a tissue sample, the system including: one or more processors; and an electronic storage medium, wherein the electronic storage medium includes instructions that, when executed by the one or more processors, cause the one or more processors to:

execute first registration instructions including: determining a first difference between a first image and a second image wherein the first image includes an RGB image of an unstained tissue sample, wherein the second image includes an RGB image of a stained tissue sample; modifying one or more of the first image and the second image, wherein the modifying includes one or more of rotation, translation, or deformation; determining a second difference between first image and the second image; determining that the second difference between the first image and second image is within an acceptable threshold value; and generating a co-registered image pair including an unstained image and a ground truth image, wherein the unstained image includes the first image or the modified first image and the ground truth image includes the second image or the modified second image; execute a first model training process including: digitally staining the unstained image to generate a first digitally stained image; and computing a loss function, wherein the loss function considers a subset of ground truth image data and a subset of digitally stained image data considers the differences between individual pixels of the ground truth image and the first digitally stained image and differences in a spatial distribution of colors in the ground truth image and the first digitally stained image; and based at least in part on a result of the loss function, adjusting one or more weights of the model; and store a generating digital staining model in the electronic storage medium, wherein the generated digital staining model includes the one or more weights.

In some aspects, the techniques described herein relate to a system, wherein the instructions further cause the system to: execute second registration instructions including: determining a third difference between the a digitally stained image generated by the trained model and the ground truth image; modifying one or more of the unstained image and the ground truth image, wherein the modifying includes one or more of rotation, translation, or deformation; determining a fourth difference between the first digitally stained image and the ground truth image; determining that the fourth difference is less within another acceptable threshold value; and generating a second co-registered image pair including a second ground truth image including the ground truth image or the modified ground truth image and a second unstained image including the unstained image or the modified unstained image; execute a second model training process including: digitally staining the second unstained image to generate a second digitally stained image; computing a second loss function, wherein the second loss function considers a subset of second ground truth image data and a subset of second digitally stained image data; and based on a result of the second loss function, adjusting one or more weights of the model.

It is important that digital staining accurately reflect what a pathologist or other professional would observe when using conventional methods such as chemical staining, which allows pathologists and other medical professionals to apply existing knowledge and experience when analyzing samples. In some cases, it may be advantageous to use an absorption-based approach, which may provide improved performance compared to transmission-based approaches.

BRIEF DESCRIPTION OF THE DRAWINGS

These and other features, aspects, and advantages of the disclosure are described with reference to drawings of certain embodiments, which intended to illustrate, but not to limit, the present disclosure. It is to be understood that the accompanying drawings, which are incorporated into and constitute a part of this specification, are for the purpose of illustrating concepts disclosed herein and may not be to scale.

DETAILED DESCRIPTION OF EMBODIMENTS

Figure 1:
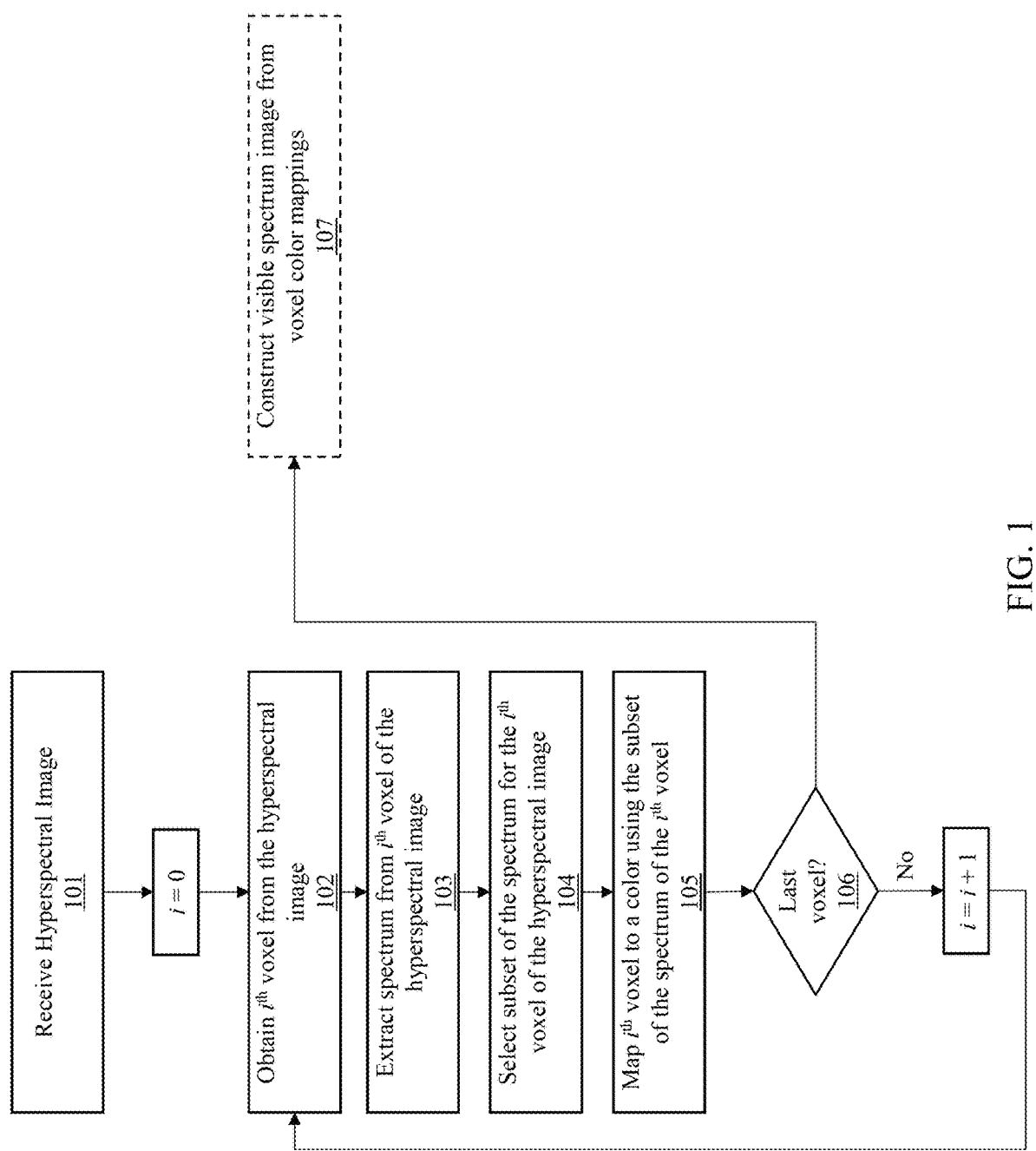
FIG. 1 illustrates a block diagram illustrating a process for generating a visible spectrum image based on a hyperspectral image according to some embodiments.

Embodiments of the disclosure will now be described with reference to the accompanying figures. The terminology used in the description presented herein is not intended to be interpreted in any limited or restrictive manner simply because it is being utilized in conjunction with a detailed description of embodiments of the disclosure. Furthermore, embodiments of the disclosure may include several novel features, no single one of which is solely responsible for its desirable attributes or essential to practicing the embodiments of the disclosure herein described. For purposes of this disclosure, certain aspects, advantages, and novel features of various embodiments are described herein. It is to be understood that not necessarily all such advantages may be achieved in accordance with any particular embodiment. Thus, for example, those skilled in the art will recognize that one embodiment may be carried out in a manner that achieves one advantage or group of advantages as taught herein without necessarily achieving other advantages as may be taught or suggested herein.

While references to voxels and 3D imaging techniques are made throughout this specification, the systems and methods described herein are equally applicable to 2D imaging unless context would clearly dictate otherwise. For example, the techniques herein could be applied to 2D microscopic images, 2D radiological images, and so forth.

As mentioned above and as will now be explained in more detail and with reference to the drawings, this disclosure includes descriptions of systems and methods for analyzing imaging data (e.g., medical imaging data) such as microscope images (e.g., RGB images), multispectral images, hyperspectral images, magnetic resonance spectroscopy images, dual-energy computed tomography (CT) scans, ultrasound images, Raman spectroscopy data, 3D images obtained by capturing a sample at a plurality of focal lengths, and so forth. The systems and methods described herein may offer significant advantages that aid in the detection and diagnosis of medical conditions, although the systems and methods herein are not necessarily limited to medical applications.

Traditional medical imaging methods offer limited information to pathologists, radiologists, and other medical professionals. For example, in traditional tissue staining and tagging, pathologists use various stains or tags to enhance the contrast between tissue components and thereby improve visibility, enabling them to distinguish between different tissues, cell populations, or organelles within individual cells. However, as mentioned briefly above, this method is limited because a single tissue sample can generally only undergo a single staining or tagging, so multiple samples may be required to use more than one stain or tag. Moreover, traditional tissue staining and tagging techniques are limited by the availability of suitable stains and tags, and there may not be a stain or tag available that can be used to reliably identify features of interest in a tissue sample. In some embodiments, the systems and methods herein can alleviate some or all of these limitations, as actual staining or tagging may not be necessary. In some embodiments, the systems and methods herein can enable the identification of features of interest without any need for physically or chemically altering a sample.

Similarly, traditional CT scanning often offers limited information. In traditional scanning, x-rays pass from a source, through the patient, and are detected by an x-ray detector. The x-ray source, which may be, for example, an x-ray tube, may emit radiation across a range of wavelengths. Each voxel in a CT scan, however, may be assigned a single value based on the attenuation of the x-ray intensity at that location. This can significantly limit the utility of CT scans because different tissues may have similar x-ray absorption properties, making it difficult or impossible to distinguish between tissue types. By collecting additional data, it may be possible to distinguish between tissue types. For example, photoelectric scattering is highly dependent on atomic number and is the predominant attenuation mechanism at low x-ray energies, while Compton scattering, which does not depend strongly on atomic number, is the predominant mechanism at higher x-ray energies. Thus, it may be possible to distinguish between tissue types by collecting data at relatively high and relatively low energies. Data may be collected by using two x-ray sources at different energies or by switching a single source between different peak kilovoltages (kVp). Alternatively, a single x-ray tube may be used in combination with a detector that is capable of differentiating between x-rays of different energies.

Technological advancements have made it possible to collect significantly more data than was possible in the past, and, in some cases, to replace or enhance traditional analytical techniques. For example, hyperspectral imaging may be used to collect information from tissue samples, providing information over a much greater range of wavelengths than imaging in the visible spectrum, and this information may be used to enable improved analysis methods. For example, instead of applying a chemically or physically staining or tagging a tissue sample, the unstained tissue can be scanned, and stains may be applied virtually. Hyperspectral data can be analyzed, and—based on the hyperspectral data—images can be produced that mimic the results of physical staining of tissue samples with a high degree of accuracy suitable for use in medical diagnostics. Moreover, because analyzing hyperspectral data is non-destructive, multiple stains can be simulated to identify multiple features of interest in a single tissue sample, eliminating the need to prepare multiple tissue slides. Additionally, new types of stains can be developed that do not have physical counterparts, allowing for the identification of features that would be difficult or even impossible using traditional staining techniques.

While hyperspectral data processing can enable a broad range of analysis, the cost of acquiring hyperspectral data can be a significant barrier. Technology advances, as described herein, can enable accurate digital staining of unstained tissue images captured using conventional cameras with red, green, and blue channels.

It will be appreciated that the examples above are merely examples, and the systems and methods described herein may be applied to other imaging and spectroscopy techniques. As just one example, the systems and methods described below may be used to analyze metabolites in tissue using data obtained from magnetic resonance spectroscopy.

Hyperspectral imaging, multispectral imaging, dual-energy CT scanning, magnetic resonance spectroscopy, and so forth may contain a significant amount of information that is not readily interpretable by a human. For example, hyperspectral or multispectral images may contain data outside the visible spectrum, and even within the visible spectrum, a human observer may not be able to readily distinguish between the narrow wavelength bands of a hyperspectral image, where the step size may be as small as 1 nm or less, or a multispectral image, which may have steps as small as 20 nm or less. For CT scans, a limited number of projections are used to reconstruct an image of the object that can be viewed by a person. For dual-energy CT scans, additional complications may arise in transforming the raw data into human interpretable forms. Even if imaging data is easily interpreted by a human, such as a visible image of unstained tissue captured using an RGB camera, the data may not be presented in a way that provides practitioners with key insights. For example, an RGB image of a tissue slide provides a practitioner with limited information. For example, practitioners may not be able to distinguish between cell nuclei and extracellular matrix in an image of an unstained tissue sample. Computational methods can enable practitioners to more fully take advantage of available data.

Analysis is commonly done using the human-interpretable representations of data. For example, analysis may be performed on a stained (or virtually stained) slide by examining only the virtually stained image and, for example, identifying features in the image. Such an approach can provide useful insight but is considerably limited because it ignores much of the available data. For example, in the case of a hyperspectral image of a tissue slide, a visible representation may only include a small fraction of the total data. In some cases, 70%, 80%, 90%, or more of the data may be discarded to generate a down-sampled image that contains visible red, green, and blue (RGB) (or cyan, magenta, yellow, and black (CMYK) or the like) values rather than the full hyperspectral dataset. Similarly, data may be lost or discarded when raw CT scan data is converted into human-readable formats.

Analysis Platform

In some embodiments, an analysis platform retains and can utilize all or at least a significant portion of the raw data from a medical imaging and/or spectroscopy data. For example, by examining the spectrum of each voxel in a hyperspectral image, it may be possible to identify features within the image or to digitally stain an image. For example, an analysis platform may be able to digitally apply a hematoxylin and eosin stain to a hyperspectral image based on the hyperspectral data. In addition to applying virtual analogs of traditional real-world stains, a platform may be able to identify other features in the hyperspectral data that are of significance. For example, there may be a signature of a particular type of protein, cell, or the like such as, for example, a spike protein that could indicate infection with a coronavirus, retrovirus, and so forth. Similarly, an analysis platform may be able to identify different compositions in dual-energy CT scan data by comparing attenuation at various wavelengths. While raw image data may be preferable for an analysis platform, it will be appreciated that, in some cases, downsampled data may be used to improve the performance of the analysis system, reduce storage space requirements, and so forth. For example, in some embodiments, an image captured over a broad spectrum can be reduced to an image containing only red, green, and blue values. In some embodiments, the resolution of imaging or spectroscopic data can be reduced. For example, an image can be reduced in resolution by combining a 2×2 pixel square into a single pixel. The single can have, for example, the average values of the 2×2 pixels from which it was created. In some embodiments, spectral data can be reduced by, for example, eliminating the data for some wavelengths. For example, regions in a spectrum that are not expected to contain useful information can be removed, or a step size can be increased by, for example, dropping every other data point, dropping every third data point, and so forth. In some embodiments, the raw data itself can be relatively limited. For example, instead of a hyperspectral or multispectral image, and image may be an image in the visible spectrum with only a limited number of channels, for example an RGB image comprising red, green, and blue channels.

In some embodiments, an analysis platform may perform analysis on raw data, downsampled data, or both and provide human-interpretable representations of the data to users of the analysis platform. In some embodiments, the analysis platform may perform relatively simple transformations to the raw data, such as, for example, selecting a subset of wavelengths from a hyperspectral image and converting the subset into visible RGB values for display (for example, by applying a constant scaling factor to each subset), or determining a reconstruction for a CT scan based on single attenuation values at each voxel. In some embodiments, the analysis platform may perform more complex transformations, such as applying a virtual stain to a hyperspectral image or an RGB image or generating a color-coded CT scan image that differentiates between different tissue types.

Advantageously, the analysis platform may be used to speed practitioner review by highlighting areas of interest, identifying substances, identifying features in images, and so forth. For example, in the case where spectral data has been captured, a practitioner may use the platform to confirm a cell type by analyzing the spectral data associated with the cell. In some cases, the analysis platform may help a practitioner to identify compositions, cell types, structures, medical conditions, and so forth. In some embodiments, analysis can be based on spectral data. In some embodiments, analysis can be based on, for example, edge detection, shape, size, and so forth.

In some embodiments, the analysis platform may run locally, for example on a practitioner's computer. Alternatively or additionally, the analysis platform may be run on a remote server that may be operated by a healthcare provider, a laboratory provider, an imaging service provider, and so forth. For example, an imaging service provider can provide a platform that can be used for processing and/or analyzing data, for example via a web application, electron application, native application, and so forth.

In some embodiments, an artificial intelligence/machine learning (AI/ML) model may be trained to identify features in raw imaging data, in downsampled imaging data, in spectral data (e.g., Raman spectroscopy data), and so forth. For example, an AI/ML model may be trained to identify features in spectral data associated with a particular voxel that may indicate a composition of the material in the voxel. For example, an AI/ML system may be able to identify lipids, nuclei, carbohydrates, and so forth based on captured spectral data. In some embodiments, an A/MLI system may be trained to identify features based on shapes in an image. In some embodiments, the AI/ML model may be configured to recommend transformations to apply to the image. For example, based on the features of the raw or downsampled data, the AI/ML model may recommend that certain virtual stains be applied to a hyperspectral image, may recommend transformations to apply to a dual-energy CT scan to highlight certain features, may recommend transformations that highlight certain metabolites in a magnetic resonance spectroscopy scan, and so forth. The AI/ML system may be trained using information about various medical conditions to determine that features observed in spectral data or in visual projections of spectral data are indicative of certain medical conditions.

In some embodiments, an AI/ML model may be trained to determine downsampling transformations that can be used to reduce image or spectroscopy file sizes without compromising the ability to perform analysis. For example, the AI/ML model may be trained to identify regions in hyperspectral imaging data that do not contain information that could be used for image analysis, such as wavelength ranges that do not show peaks in transmission or absorption. Thus, for example, the storage space required to store images, spectroscopy data, or both may be reduced. The computational resources required to process images and other data can be lessened without losing important information.

In some embodiments, a user of the analysis platform may request an initial transformation, such as a virtual stain, and the platform may recommend additional transformations to the user or may, in some cases, automatically apply the additional transformations. In some embodiments, the user may specify a suspected condition and the analysis platform may determine transformations to apply. In some embodiments, the user may provide only raw imaging data, and the system may, based on the raw imaging data, identify one or more features of interest (e.g., cell walls, spike proteins, regions with spectral features that indicate an abnormality, and so forth), and determine one or more transformations to apply to the raw imaging data.

For example, an AI/ML model can be trained to recognize structural features, spectral features, and so forth, and to determine stains or other transformations to apply based on the recognized structural features, spectral features, or both.

In some embodiments, third parties may wish to extend the analysis platform. For example, third parties may develop new virtual stains, feature detection algorithms, visualization tools, and so forth. A third party may wish to display data in a different way or to visualize data for an imaging method that the analysis platform does not natively support. In some embodiments, the analysis platform may provide an application programming interface (API), library, or the like to allow third parties to extend the analysis platform. In some embodiments, third parties may create extensions for their own use or may make extensions available to other users of the analysis platform. In some embodiments, the analysis platform may include features to allow third parties to charge for access to extensions. For example, the platform can include an electronic store that can be used to purchase access to extensions. In some embodiments, the platform can offer access to extensions on a subscription basis. In some embodiments, the platform can offer access to extensions on a perpetual license basis. In some embodiments, access to the platform itself can be offered on a subscription basis, on a perpetual basis, or both. In the platform can include a payment system. In some embodiments, the payment system can directly collect payment information. In some embodiments, the payment system can interface with third party payment processors to facilitate payments.

FIG. 1 depicts a sample process for transforming a hyperspectral image to a visible image according to some embodiments which may be run on a system that is configured to run an analysis platform. At block 101, the system may receive a hyperspectral image. For example, a user may upload an image to the system. At blocks 102, 103, 104, and 105, the system may, for each voxel, extract the spectral data for the voxel, select a subset of the spectral data, and based on the subset of the spectral data, map the voxel to a color in the visible spectrum (for example, by determining an RGB value). In some embodiments, the system may store one or more image transformation matrices that indicate how the received image can be transformed. At decision point 106, the system may exit the loop after mapping the last voxel of the hyperspectral image and, at block 107, construct a visible image from the mapped voxel. In some embodiments, the subset selected at block 104 may be, for example, determined based on a user selection such as a drop-down menu that allows the user to select a predefined wavelength (or frequency, energy, or wavenumber) range. For example, a user may choose an option to display a representation of data in the infrared or ultraviolet regions. For example, in some embodiments, the user can select from a number of predefined wavelength regions. In some embodiments, the user may specify starting and stopping wavelengths, wavenumbers, frequencies, or energies. In some embodiments, the user can save configuration data (e.g., wavelength ranges) for use again in the future. In some embodiments, the user can share the configuration data with other users, for example with other users in the user's organization or more broadly. In some embodiments, the system may have additional features. For example, the color map may be modified based on a user's request to modify contrast, brightness, or to apply a different mapping. As just one example, a user may wish to modify the mapping so that a particular wavelength range of interest stands out in the constructed visible spectrum image.

While FIG. 1 illustrates the transformation of a hyperspectral image into a visible image based on a subset of the hyperspectral data, the skilled artisan will recognize that a similar approach may be used to visualize other types of data. For example, instead of receiving a hyperspectral image at block 101, a system could receive dual-energy CT scan data and map said data into a visible representation or could receive an RGB image and operate on the red, green, and blue channels of the image. In some embodiments, the system could receive magnetic resonance spectroscopy data and map said data into a visible representation. Subsets of the spectral data and color mappings could be chosen based on, for example, a particular metabolite of interest.

Figure 2:
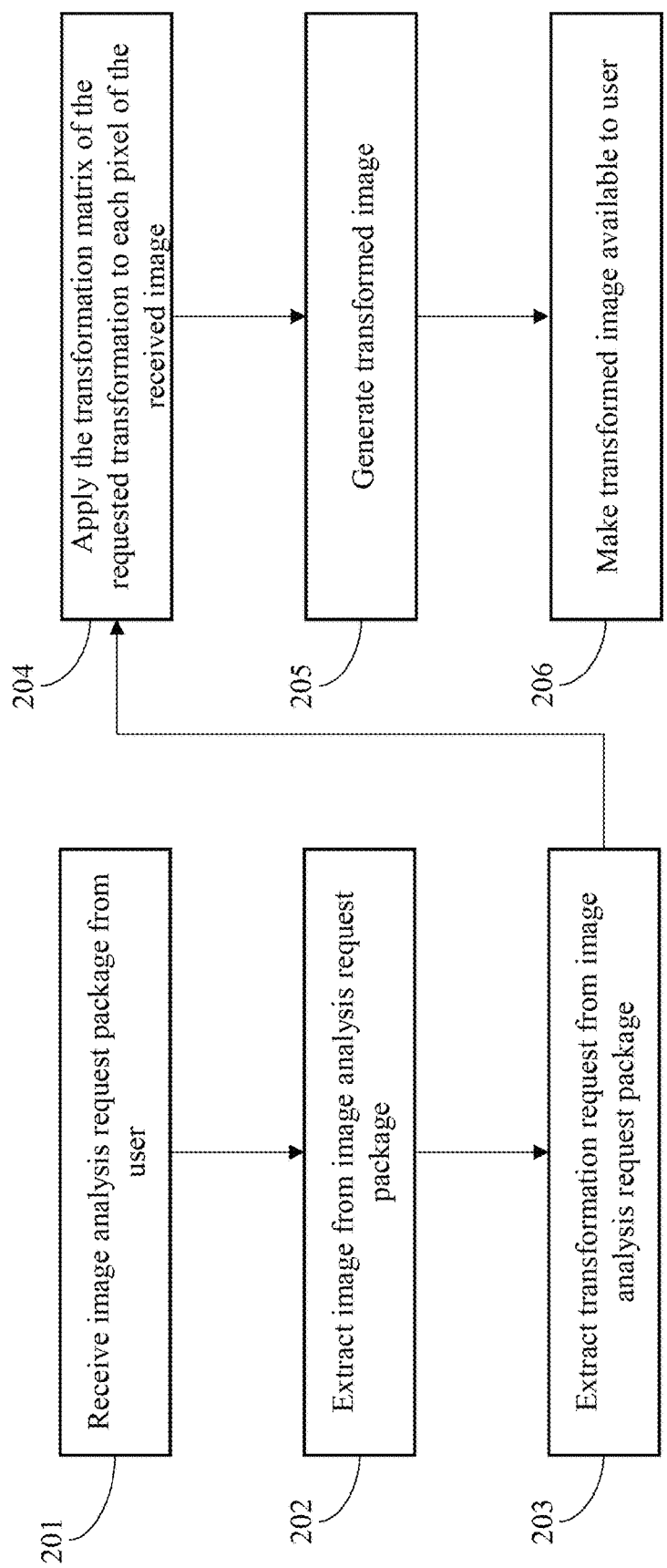
FIG. 2 illustrates a block diagram that depicts an analysis process according to some embodiments.

FIG. 2 is a block diagram that depicts an analysis process according to some embodiments. A computer system may be configured to execute the process depicted in FIG. 2. At block 201, the system may receive an analysis request package from a user of an analysis platform. At block 202, the system may extract an image, which may be, for example, a hyperspectral image, an RGB image, a CT scan, an Mill, a PET scan, and so forth, from the analysis request package. At block 203, the system may extract a request to apply a transformation to the image from the analysis request package. In some embodiments, the request may be, for example, to apply a virtual stain to a hyperspectral image or to apply another transformation that would be of use to a pathologist, radiologist, or the like. At block 204, the system may apply the requested transformation to each voxel of the received image. In some embodiments, applying the requested transformation may be done according to the process depicted in FIG. 1. At block 205, the system may generate a new transformed image based on the results of transforming each voxel in the received image. At block 206, the system may make the transformed image available to the user.

In some embodiments, rather than receiving an analysis request package from the user, the system may receive an image from the user and may separately receive instructions or requests to perform transformations on the received image. For example, a user may upload an image to the system and may select one or more transformations to apply via a user interface of the system such as, for example, a computer program in communication with the system or a website or web application controlled by the provider of the analysis platform. In some embodiments, an imaging system (e.g., a computer system associated with an imaging device) can be configured to upload imaging data automatically, manually, or both to the analysis platform. In some embodiments, a user may select for analysis one or more images that have been uploaded to the analysis platform.

Figure 3:
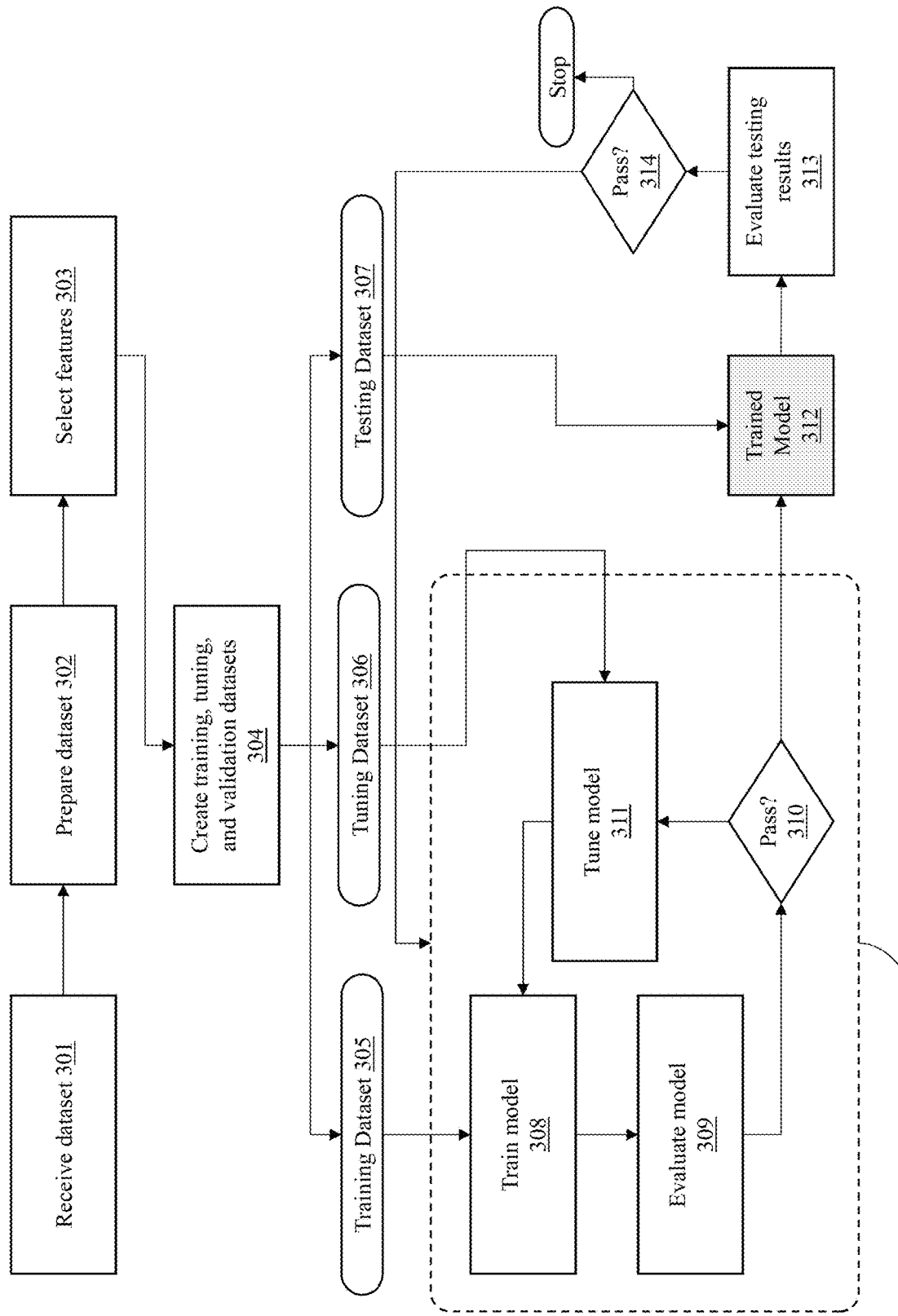
FIG. 3 illustrates a block diagram illustrating a process that may be run on a computer system to train a machine learning model.

In some embodiments, the analysis platform may make additional functionality available to users of the platform. For example, the analysis platform may use artificial intelligence or machine learning (AI/ML) models to detect features, identify potential conditions, recommend additional imaging analysis, and so forth. FIG. 3 is a block diagram illustrating a process that may be run on a computer system to train a machine learning model. At block 301, the system may receive a dataset which may be, for example, a set of hyperspectral tissue images, a set of CT scans, a set of RGB images, or the like. At block 302, one or more steps may be performed to prepare the dataset such as, for example, removing duplicates, adding or modifying metadata (for example, an image may be tagged as corresponding to a diagnosis of a type of cancer), and so forth. At block 303, the system may receive one or more features of interest. For example, the system may be configured to identify image regions that have particular spectral characteristics, shapes, and so forth. At block 304, the system may create, from the received dataset, training, tuning, and testing datasets. The system then, in training loop 315, trains the model at block 308 using the training dataset block 305. Training may be conducted in a supervised, unsupervised, or partially supervised manner. At block 309, the system may evaluate the model according to one or more evaluation criteria. For example, the evaluation may include false positive rates, false negative rates, true positive rates, true negative rates, and so forth. At decision point 310, the system may determine if the model meets the one or more evaluation criteria. If the model fails evaluation, the system may, at block 311, tune the model using the tuning dataset block 306, repeating the training block 308 and evaluation block 309. Once the model passes the evaluation at 310, the system may exit the model training loop 315. The testing dataset 307 may then be run through the trained model 312 and, at block 313, the system may evaluate the results. If the evaluation fails (for example, by having an unacceptable false positive or false negative rate), at decision point 314, the system may reenter training loop 315 for additional training and tuning. If the model passes, the system may stop the training process, resulting in a trained model 312.

Figure 4:
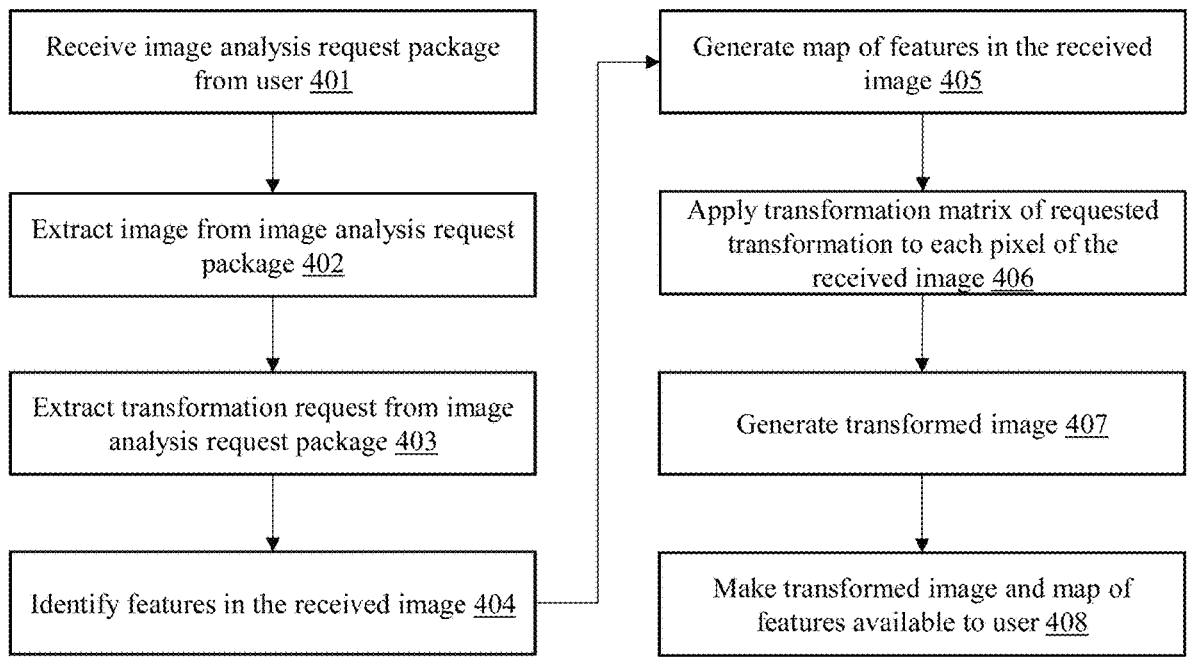
FIG. 4 illustrates a block diagram illustrating a process for generating an image feature map according to some embodiments.

In some embodiments, the analysis platform may use an AI/ML model or another suitable algorithm to identify and label features in an image. FIG. 4 is a block diagram illustrating a process that may be implemented on a computer system for generating an image feature map according to some embodiments. At block 401, a system may receive an image analysis request package from a user of the system. At block 402, the system may extract image data from the analysis request package. The image may be, for example, a hyperspectral image, a traditional CT scan with only a single value for each voxel, a dual-energy CT scan, a multispectral image, an RGB image, a magnetic resonance spectroscopy image, and so forth. At block 403, the system may extract from the analysis request package a request to apply a transformation to the received image. At block 404, the system may, using an artificial intelligence model or other method, identify one or more features (e.g., compositions, shapes, and so forth) in the received image data, based on the received image data. At block 405, the system may generate a map of features in the received image data. At block 406, the system may apply the requested transformation to each voxel of the received image data to, at block 407, generate a new transformed image for viewing by the user. At block 408, the transformed image may be made available to the user along with the feature map that was determined from the received image data. In some embodiments, the feature map may be presented as an overlay to the generated images which may be turned on or off by the user. For example, the feature map may comprise labels, circles, rectangles, colored regions, and so forth that indicate regions of interest in the generated images.

In some embodiments, not all of the steps indicated in FIG. 4 may be performed. For example, in some embodiments, a user may submit an image for feature identification without requesting a transformation. As just one example, a user may submit a traditional CT scan that contains a single value at each voxel, and the system may identify features in the CT scan without applying a transformation to the received data (or applying only minimal transformations, such as converting absorption values to grayscale representations).

Reference is made above to image analysis request packages. In some embodiments, an image analysis request package can include image data and information indicating how the image should be processed. In some embodiments, image analysis request package contents can be received separately. In some embodiments, the request package can include one or more images. In some embodiments, the request package can include a request to perform an analysis on one or more images that have been previously uploaded to the analysis platform. In some embodiments, rather than or in addition to an image, a spectrum or other data can be supplied to the platform. In some embodiments, the request package can include multiple images or spectra and can include instructions to apply to each, which can be different or the same.

In some embodiments, the system may detect features based on processed representations of images rather than from raw image data, although this may not be preferred because having only a subset of the raw data or a representation of a subset of the raw data limits the information available to the system to perform feature detection, which may prevent the system from identifying features that were present in the raw data but not in the processed representation. While more data may generally be preferable, it will be appreciated that useful analysis can be performed on a wide variety of images, including RGB images, which can enable greater access to imaging analysis, especially in cases where the cost of high-end imaging equipment such as hyperspectral imaging systems is a significant barrier to access.

Figure 5:
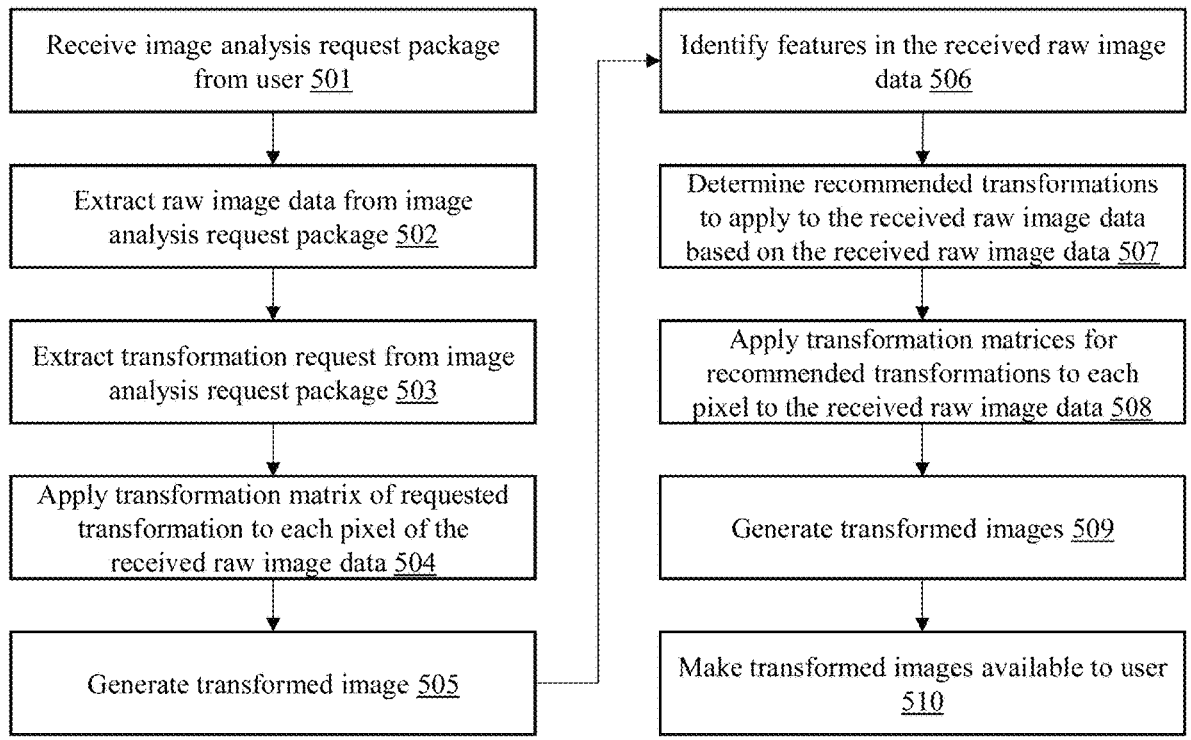
FIG. 5 illustrates a block diagram illustrating a process for applying image transformations based on feature identification according to some embodiments.

In some embodiments, the analysis platform may be configured to determine transformations to apply based on analysis of received raw data (although, as mentioned above, in some embodiments, raw data may not be used). FIG. 5 is a block diagram illustrating a process that may be run on a computer system for applying image transformations based on feature identification according to some embodiments. At block 501, a system may receive an image analysis request package from a user of the system. At block 502, the system may extract an image from the analysis request package. The image may be, for example, a hyperspectral image, a dual-energy CT scan, a multispectral image, a magnetic resonance spectroscopic image, and so forth. At block 503, the system may extract from the analysis request package a request to apply a transformation to the received image. At block 504, the system may apply the requested transformation to the image in order to, at block 505, generate a new transformed image. At block 506, the system may identify features in the received image data using an artificial intelligence model, such as the trained model 312, or by using other suitable techniques. At block 507, the system may, based on the identified features in the received image data, determine transformations to apply to the received image data. For example, if the received image data has indications of cancer, the system may recommend additional transformations that may, for example, help to identify the type of cancer, help distinguish between cancerous and health tissue, and so forth. Alternatively, or additionally, the system may recommend additional transformations based on the transformation request received from the user. For example, if a user requests a particular virtual stain to be applied to a hyperspectral image, the system may recommend additional virtual stains based on the requested virtual stain. At block 508, the system may, either in response to a request from the user or automatically, apply the recommended transformations to each voxel of the received image. At block 509, the transformed voxels may be used to generate new transformed images. At block 510, the generated new images may be made available to the user of the system. In some embodiments, not all the steps in FIG. 5 may be performed. For example, a user may not include a request to apply a transformation. In such a case, the system could determine recommended transformations based on identified features in the received raw image data, but would not perform the steps in blocks 503, 504, and 505.

Figure 6:
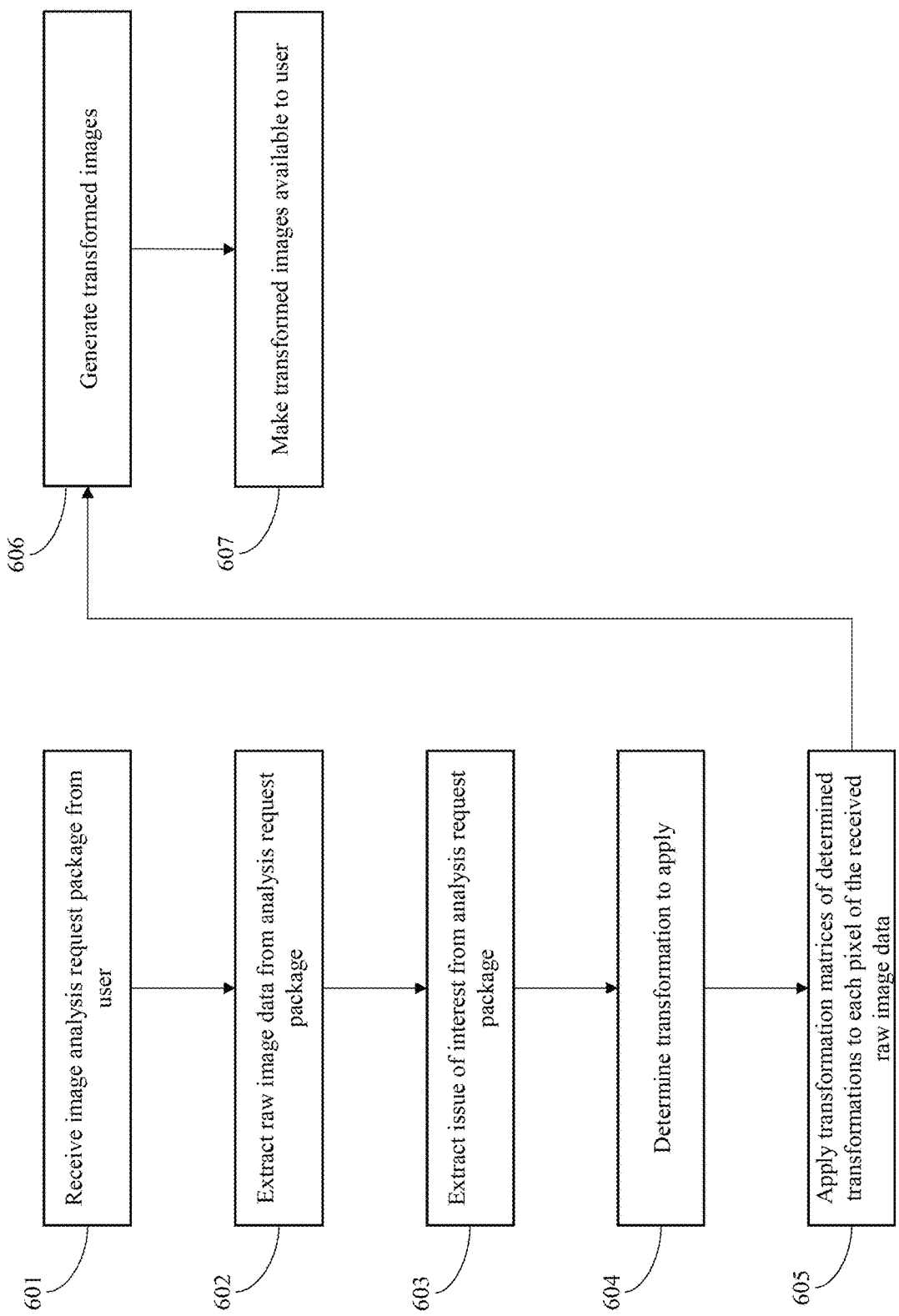
FIG. 6 illustrates a block diagram illustrating a process for applying image transformations based on a specified condition according to some embodiments.

In some embodiments, rather than (or in addition to) specifying a transformation to apply, a user of the analysis platform may specify a condition or issue of interest. For example, a user may be looking for a certain type of cancer, trying to identify particular metabolic pathways, looking for infection with a particular type of virus, and so forth. FIG. 6 is a block diagram illustrating a process that may be run on a computer system to apply image transformations based on a specified condition according to some embodiments. At block 601, the system may receive an image analysis request package from a user of the system. At block 602, the system may extract raw image data such as a hyperspectral image, dual-energy CT scan, or the like, from the analysis request package. At block 603, the system may extract an issue of interest from the analysis request package, which may be, for example, a request to look for cancers, viruses, metabolic issues, and so forth. At block 604, the system may determine, based on the issue of interest, at least one transformation to apply to the image data. At block 605, the system may apply the at least one transformation to each voxel of the image data. At block 606, the system may generate at least one transformed image based on the at least one transformation applied to the image data. At block 607, the system may make the at least one new transformed image available to the user.

An extensible platform may be advantageous in some embodiments. For example, a platform provider may make available core functionality for working with imaging data such as visible spectrum images, hyperspectral images, magnetic resonance spectroscopy images, dual-energy CT scans, and so forth. For example, the platform provider may make available tools for common tasks such as virtually staining images using common stains or for transforming CT data to distinguish between tissue types. The platform provider may also provide a set of analysis tools, such as feature identification, labeling, automated navigation (e.g., automatically directing a user to image regions that contain features of interest), and so forth. In some embodiments, the platform provider may make the platform open to third parties. Third parties may, for example, develop new virtual stains which may or may not exist in nature, develop transformations for other imaging techniques, build new analysis tools, and so forth. For example, third parties may wish to develop new transformations or tools for use in research or to aid in detecting emerging conditions. In some cases, third parties may wish to make transformations and analytical functions available only to themselves, or they may wish to make transformations and analytical functions available to other users of the analysis platform, either for free or for a fee, which could be a one-time fee or an ongoing subscription fee.

Figure 7:
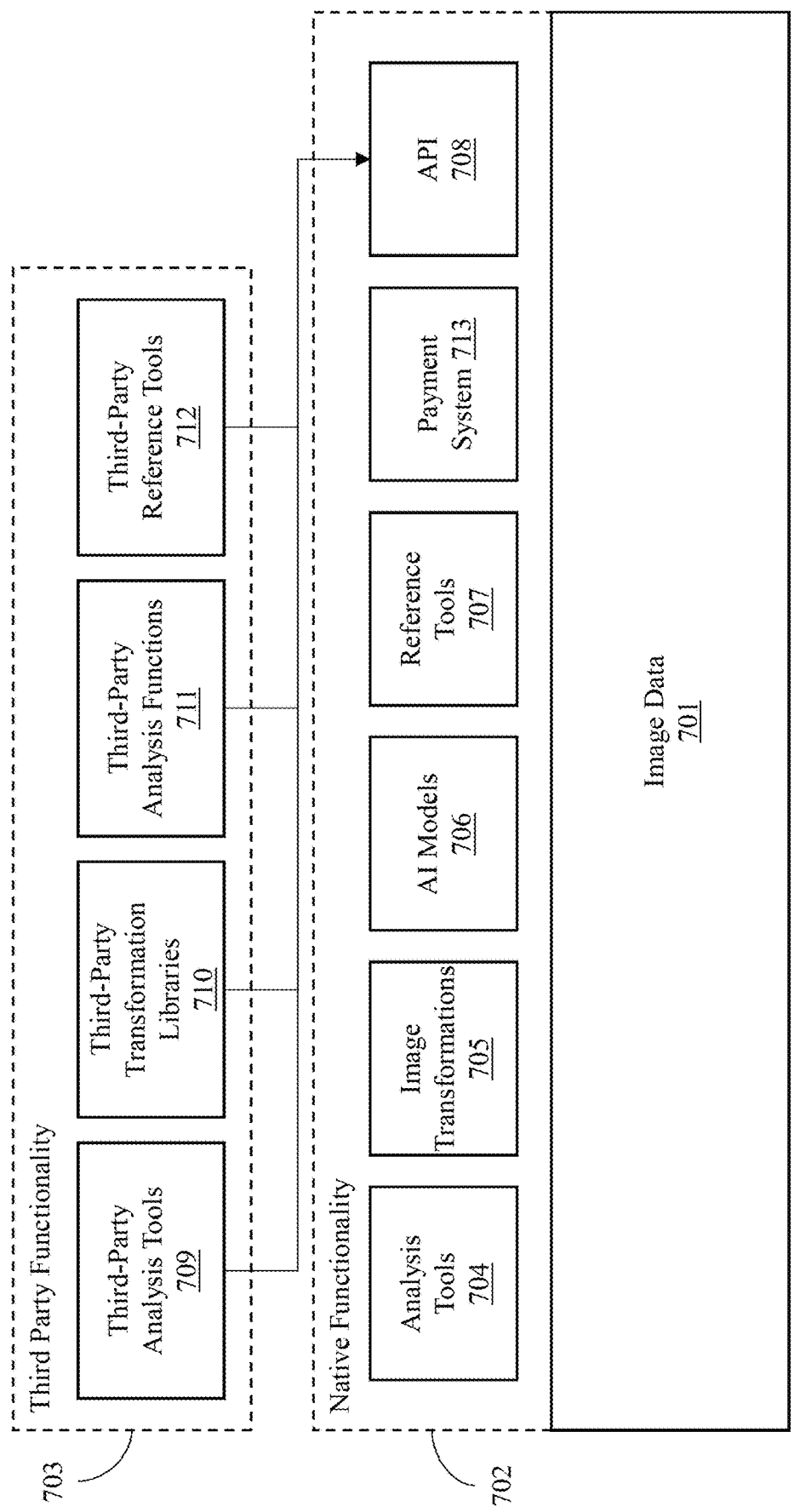
FIG. 7 illustrates a block diagram that illustrates an extensible platform according to some embodiments.

FIG. 7 illustrates an extensible platform according to one embodiment. Image data 701, such as hyperspectral image data, CT data, and so forth, may be manipulated using native functionality 702, which may include analysis tools 704, image transformations 705 and AI models 706 (such as the trained model 312), although other features may also be included in the native functionality 702. For example, the native functionality may also include reference tools 707 which may, for example, be configured to provide information to a user of the platform based on the analysis. For example, the reference tools 707 may show example images, provide information about a condition, explain how different stains may be used to identify a condition, and so forth. In some embodiments, the platform can include a payment system 713.

The native functionality 702 includes an application programming interface 708 or some other means to allow third parties to interact with the platform. Third parties may build third-party functionality 703, which may include third-party analysis tools 709, third-party transformation libraries 710, third-party analysis functions 711, and third party reference tools 712. In some embodiments, only a subset of third-party functionality may be available, or additional third-party functionality may be made available. The third-party transformation libraries 710 may comprise, for example, new virtual stains for hyperspectral images, new transformations for magnetic resonance spectroscopy images, and so forth. The third-party analysis functions 711 may integrate with native analysis tools made available by the platform provider.

In some cases, third parties may provide third-party analysis tools 709 which operate at least partially independently of the tools provided by the platform provider. For example, an analysis function may work as a plugin to existing tools (e.g., the analysis tools 704 provided by the platform provider), while a third-party analysis tool 709 may be a separate application.

Figure 8A:
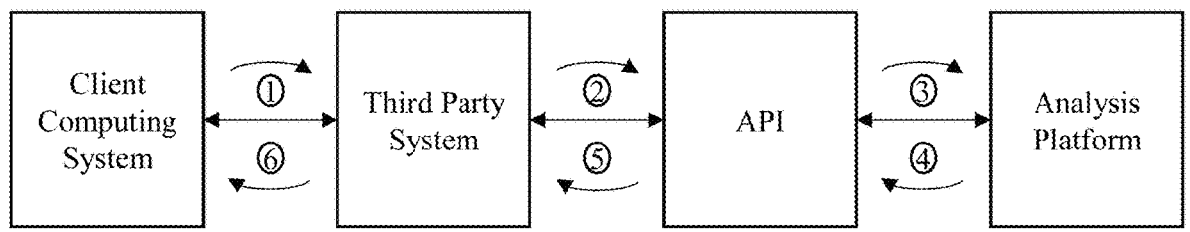
FIGS. 8A and 8B are block diagrams that illustrate examples of using an analysis platform in conjunction with third party systems according to some embodiments.
Figure 8B:
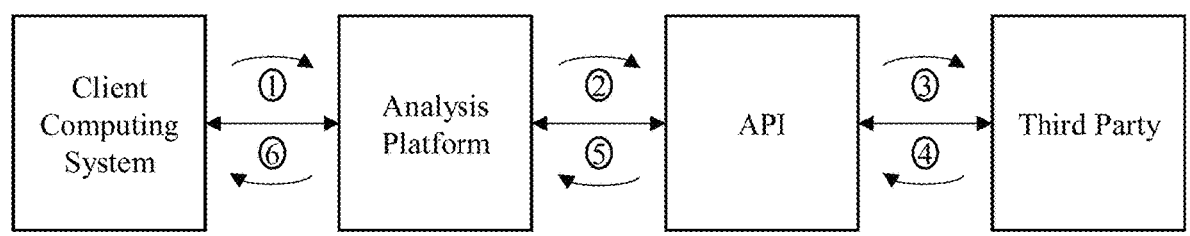

FIGS. 8A and 8B illustrate examples of using an analysis platform in conjunction with third party systems according to some embodiments. As shown in FIGS. 8A and 8B, there are various approaches for taking advantage of third party systems. In FIG. 8A, a client interacts directly with the third party system. Such an approach might be used where, for example, a third party has developed software (e.g., a web application, native application, etc.) to be used directly by clients. In FIG. 8A, at circle 1, a client computing system interfaces directly with a third party system, for example using an application provided by the third party. In some embodiments, the third party system can perform processing on data received from the client computing system. In some embodiments, the processing can be performed according to processing instructions provided by the client computing system. In some embodiments, the processing can be performed by the third party system without specific instructions from the client computing system. At circle 2, the third party system using an API to construct relevant calls to functionality of the analysis platform. At circle 3, the analysis platform receives the API calls. The API calls can include, for example, calls to perform particular operations on data supplied by the third party system. At circle 4, the analysis platform can prepare the results and pass them to the third party system using the API. At circle 5, the third party system can receive the results using the API. In some embodiments, results can be automatically pushed to the third party system. In some embodiments, the third party system can execute a second API call or set of API calls to retrieve the results from the analysis platform. At circle 6, the third party system can provide the results to the client computing system. In some embodiments, the third party system can automatically provide the results to the client computing system. For example, the third party system can push the results to the client computing system. In some embodiments, the third party system can be configured to provide the results to the client computing system after receiving a request for the results from the client computing system. In some embodiments, the third party system can perform processing on the results prior to providing the results to the client computing system.

While FIG. 8A depicts a scenario in which a client computing system interacts directly with a third party system, other implementations are possible. For example, in some cases, a third party may not implement a user interface, or may wish to offer only a limited user interface, such as a configuration panel or the like, that can be integrated into an interface provided by the analysis platform. In FIG. 8B, at circle 1, a client computing system interfaces directly with an analysis platform. For example, the client computing system can provide an image or other data to the analysis platform. In some embodiments, the client computing system can provide a request for performing particular processing to the analysis platform. In some embodiments, some or all of the processing can be performed by a third party. In some embodiments, the analysis platform can perform processing prior to sending a processing request to the third party system. At circle 2, the analysis platform can use an API to send a processing request to the third party system. At circle 3, the third party system can receive the processing request. In some embodiments, the processing request can specify data on which processing is to be done and instructions for processing steps to be completed by the third party system. The third party system can perform processing on the data according to the instructions received from the analysis platform using the API. At circle 4, the third party system can make results of the processing available to the analysis platform using the API. In some embodiments, the third party system can push the results to the analysis platform. In some embodiments, the analysis platform can request the results from the third party system via the API. At circle 5, the analysis platform can receive the results from the third party. In some embodiments, the analysis platform can perform additional processing. At circle 6, the analysis platform can provide results to the client computing system. In some embodiments, the analysis platform can push the results to the client computing system. In some embodiments, the client computing system can request the results from the analysis platform. In some embodiments, the analysis platform can provide a notification to the client system that results are available.

Figure 9:
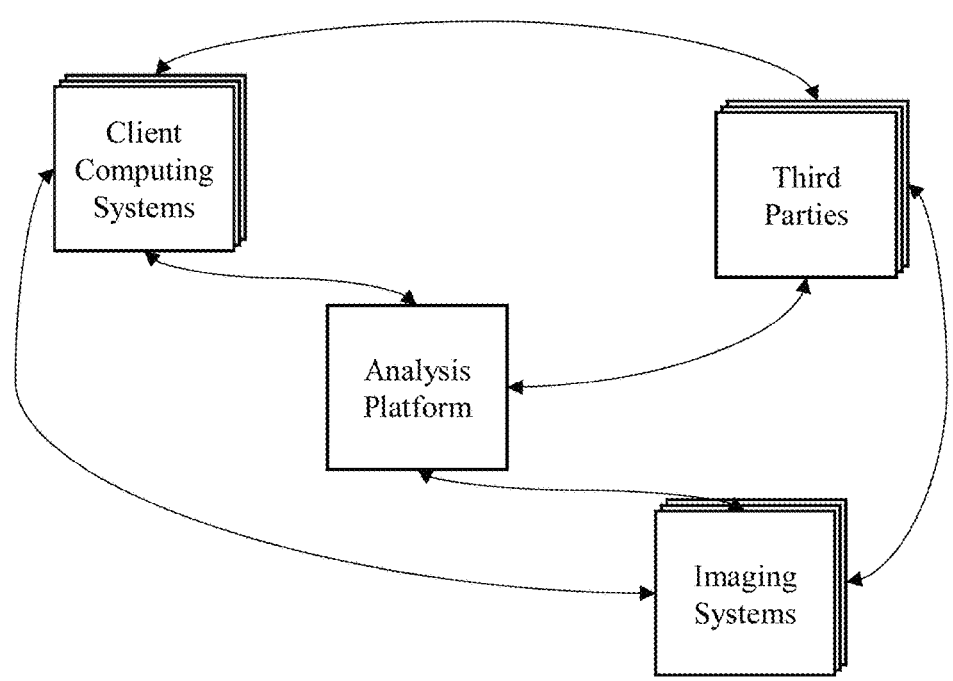
FIG. 9 illustrates examples of communication that can occur between different systems in some embodiments.

FIG. 9 illustrates examples of communication that can occur between different systems. Systems can include client computing systems, third party systems, imaging systems, and an analysis platform. These are merely non-limiting examples. In some embodiments, not all systems may be present. In some embodiments, additional systems that are not illustrated can be present. As illustrated in FIG. 9, the systems can communicate directly with each other or via the analysis platform. For example, an imaging system such as a microscope can be networked such that it can communicate directly with an analysis platform, third party, or client computing system. In some embodiments, the imaging system may not be connected to a network and thus may be unable to directly communicate with other systems. For example, an imaging system can store data on a removable storage medium that can later be connected to a client computing system, and the client computing system can communicate with the analysis platform, third party systems, or both.

Real-Time Digital Staining

The examples described above can enable powerful processing and analysis of imaging and other medical data. However, the above examples may typically (though not necessarily) be used after imaging data is fully captured. In some cases, an image may not provide useful information, for example due to a lack of relevant features in the image. Thus, it can be advantageous to provide for some degree of real-time processing (e.g., real-time, or substantially real-time, digital staining). This can enable practitioners to quickly recognize if an image capture will be useful or if an image capture is unlikely to produce useful results, in which case the practitioner can abandon the capture process and adjust their procedure accordingly, for example by adjusting image capture parameters (e.g., exposure time), by moving to a different area on a slide, by preparing a sample (e.g., a new tissue slide), and so forth.

Accordingly, some embodiments herein are directed to systems and methods that can enable real-time digital staining. As used herein, real-time or substantially real-time means within a short period of time, such as within half of a second, within 1 second, within 2 seconds, within 3 seconds, within 4 seconds, within 5 seconds, etc. Some delay for processing is anticipated and expected, so long as the delay is sufficiently short such that a practitioner can review and make decisions based on a digitally stained image before an unstained image is fully captured.

Real-time digital staining can be especially useful in the case of multispectral or hyperspectral imaging, which can take a significant amount of time to capture. For example, an image capture process can take several minutes (e.g., 5 minutes, 10 minutes, 15 minutes, etc.), depending upon various factors such as the size of the field being captured, the exposure time, the wavelength range of the capture, the wavelength step size, number of bands, and so forth.

Figure 10:
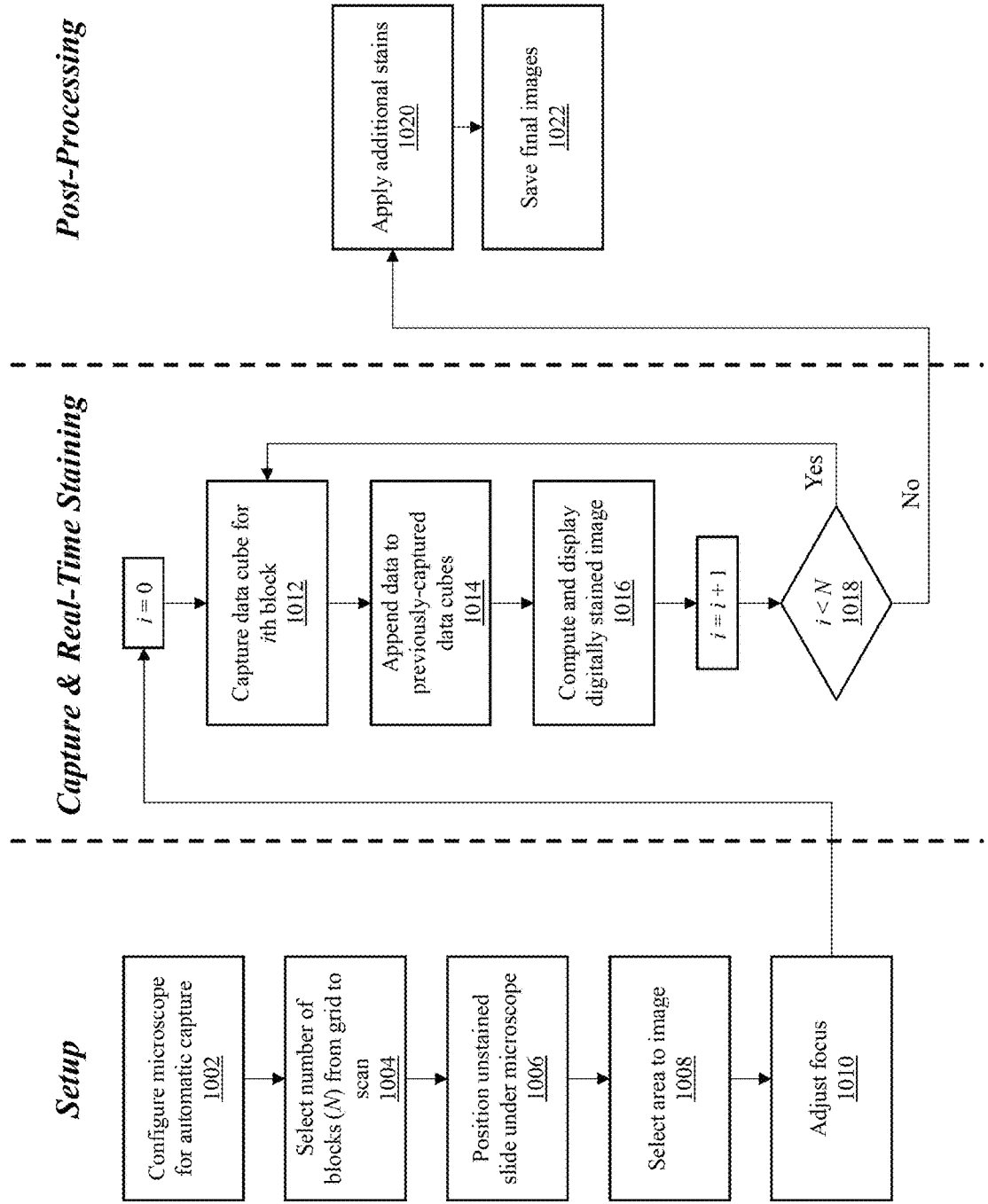
FIG. 10 is a block diagram illustrating an example process for performing real-time staining according to some embodiments.

FIG. 10 depicts a process for real-time digital staining according to some embodiments. In a setup phase, at block 1002, a user may configure a microscope for automatic image capture. At 1004, the user may select a number of blocks to scan from a grid. For example, a user can select a subset of blocks from the full field of view of the microscope. At 1006, the user may place an unstained slide under the microscope in preparation for imaging the slide. At block 1008, the user may select an area to image and, at block 1010, the user may adjust the focus of the image. During a capture and real-time staining phase, a counter i may be initialized and used to count the number of blocks that have been scanned. At block 1012, a system may capture a data cube for the ith block. At block 1014, the system may append data for the ith block to previously-captured data cubes. At block 1016, the system may compute and display a digitally stained image to the user. The counter i may be increased to indicate that an additional block has been captured. At block 1016, the system may check to see if all blocks have been captured. If there are still blocks to capture, the system may repeat blocks 1012, 1014, and 1016 to capture the next block, append the next block to the previously-captured data cubes, and compute and display a digitally stained image. In some embodiments, the system may recompute the digital stain for all blocks that have been captured. In some embodiments, the system may compute the digital stain for only the most recently captured block and can append the digitally stained block to any other blocks that have already been digitally stained If, at block 1018, the system determines that there are no more blocks to capture, the capture and real-time staining phase may be complete. During a post-processing phase, the user may apply additional stains at block 1020. In some embodiments, the system may use additional stains. The stain applied at block 1016 may be, for example, a common stain such as H&E, and the additional stains applied at block 1020 may be specialized stains for differentiating lipids, muscle, organisms, minerals, and so forth. At block 1022, one or more final images may be saved. The final images may be, for example, unstained images, images digitally stained with H&E, images digitally stained with specialized stains, and so forth.

In some embodiments, the number of grids (or fields) can be defined based on the active tissue field to be imaged. For example, for a whole slide image scan at 40× magnification, a field size can be 1024×1024 pixels, representing a physical area of about 166 microns×about 166 microns. In some embodiments, there can be tens or hundreds of fields. In some embodiments, it may be desirable to reduce a number of fields. For example, for hyperspectral imaging, it may be desirable to decrease the number of fields to reduce capture times. For example, in some embodiments, an area of interest can be identified and fields can be selected that are in or near (e.g., adjacent to) the area of interest.

FIG. 10 illustrates a process using a hyperspectral line scanner. However, it will be appreciated that other imaging modalities are possible. For example, a snapshot scanner can capture an entire field at once (like an optical RGB camera). For a snapshot scanner, optical RGB camera, and the like, a block can be regarded as a full field. Each field can be processed to generate a digitally stained image, rather than a block comprises one or more lines of an image.

Figure 11:
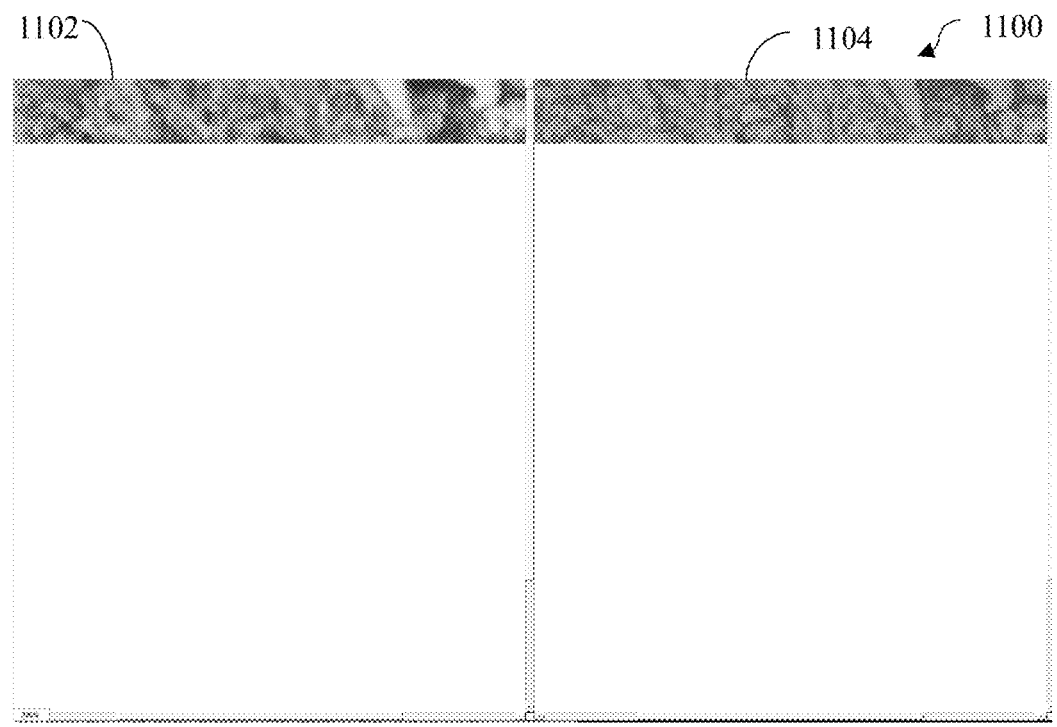
FIG. 11 illustrates an example display of stained and unstained images according to some embodiments.

FIG. 11 depicts an example interface for displaying images according to some embodiments. In FIG. 11, an image display area 1100 has a digitally stained view 1102 which corresponds to an unstained view 1104. The digitally stained view and the unstained view may, as shown in FIG. 11, depict an incomplete capture. The image display area may be updated as unstained image data becomes available or as digitally stained image data becomes available. For example, in some embodiments, the system may be configured to perform digital staining of each voxel in the image as the image is captured. In other embodiments, the system may be configured to perform digital staining periodically such as, for example, after each line is captured, after 10 lines are captured, after 20 lines are captured, and so forth. As discussed above, in some embodiments, the system can be configured to perform digital staining after each block is captured. Decreasing the number of voxels that are captured before performing digital staining may provide digitally stained image data to the user faster, but may have tradeoffs in terms of, for example, the computing power needed to compute the digitally stained image. In some embodiments, digital staining can produce better images if a greater number of voxels are captured. For example, the system can consider more spatial information if a greater number of voxels are used. In some embodiments, digital staining algorithms may expect more than a single voxel. For example, a digital staining algorithm may use information about neighboring voxels (e.g., nearest neighbors, next nearest neighbors, and so forth) to determine how a digitally stained voxel should appear.

Figure 12:
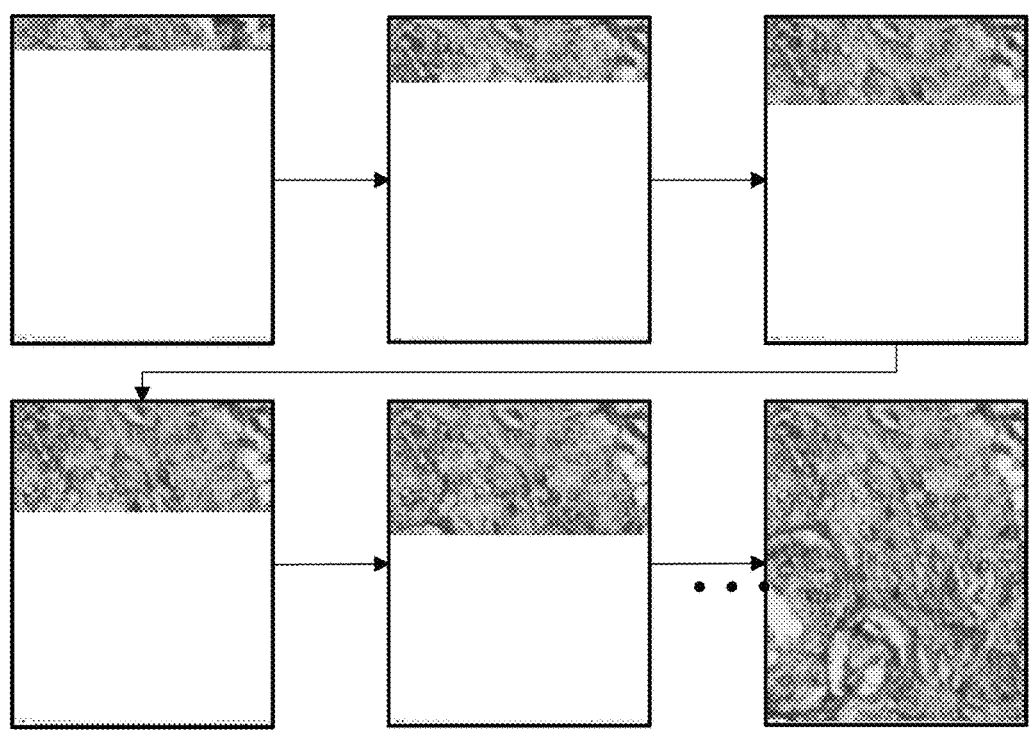
FIG. 12 illustrates an example of real-time staining according to some embodiments.

FIG. 12 depicts a real time digital staining process according to some embodiments, which may be implemented on a computer system. In FIG. 12, the image is divided into twelve horizontal slices and the system applies a digital stain to each slice as the slice is completed. The system adds each new slice to the previous slices, eventually forming the completed digitally stained image. As discussed above with respect to FIG. 11, the number of slices may be varied according to the needs of the user, the capabilities of the computing system, and/or the algorithms being used to perform the digital staining process.

Model Training and Testing

Hyperspectral microscopes provide data in the form of data cubes containing two spatial dimensions and one spectral dimension (wavelength). Generally, high resolution hyperspectral image data cubes may contain a large number of wavelengths, such as, for example, more than 300, more than 400, more than 500, and so forth. In some cases, hyperspectral imaging equipment may capture data with a wavelength resolution of, for example, about 1 nm over a wavelength range in the visible and near infrared from about 400 nm to about 1000 nm. Shortwave infrared devices may capture from about 900 nm to about 1700 nm in increments of about 5 nm. In the mid-infrared from about 2500 nm to about 13,000 nm, commercially available detectors may provide measurements with about 13 nm spectral resolution. Thus, hyperspectral images may be large and may require significant computing resources to manipulate and analyze. Additionally, because pathological tissue often contains densely formed, spatially distributed microscopic structures, neighboring pixels may contain different spectra. Thus, there is a need for a way to perform digital staining on a reduced data set without losing critical information.

Digital stains may be created by training an artificial intelligence (AI) or machine learning (ML) model to translate between an unstained image and a chemically stained image. In order to achieve real-time or near-real-time digital staining, it is advantageous to reduce the amount of data and the processing time for performing digital staining functions. This may be achieved, for example, by working with compressed or reduced datasets which transform the hyperspectral data cubes to multiband data cubes. In some embodiments, AI/ML models may be trained to translate hyperspectral images to digitally stained images by using multiband data.

Figure 13:
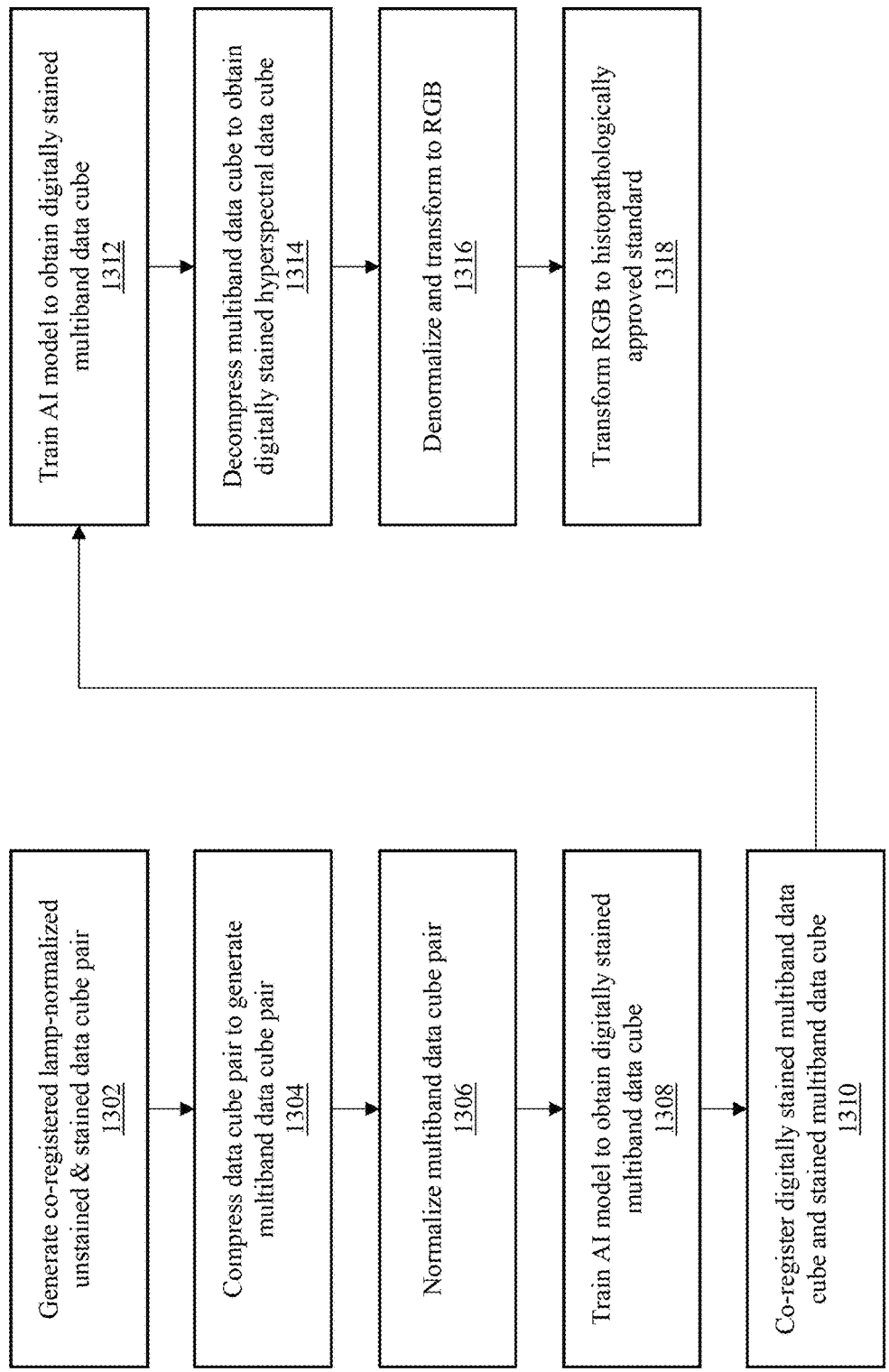
FIG. 13 is a block diagram illustrating an example process for model training and testing according to some embodiments.

FIG. 13 is an overview of a process for training and testing an AI/ML model according to some embodiments, which may be run on a computer system. At block 1302, the system may generate a co-registered, lamp-normalized (e.g., accounting for the emission properties of the light source) data cube pair from an unstained capture and a stained capture of the same tissue sample. At block 1304, the system may compress the data cube pair to generate a multiband data cube pair. At block 1306, the multiband data cube pair may then be normalized (e.g., scaled so that values range from 0 to 1 or from −1 to 1) in preparation for training an AI model. At block 1308, the system may train an AI model to obtain a digitally stained multiband data cube from an unstained multi-band data cube. That is, the system may train the AI/ML model to map an unstained multiband image to a stained multiband image. In some embodiments, a generative adversarial network may be used to generate digital stains.

While the unstained and stained images were co-registered prior to training at block 1308 the co-registration may not be exact. Errors in co-registration can have a significant impact on the performance of the AI/ML model. For example, even small differences in the locations of features within the stained and unstained images can cause significant difficulties for the AI/ML model, potentially resulting in poor performance. This can be especially problematic in the case of images of tissue samples because, as discussed briefly above, tissue samples tend to have a high density of small structures, which can cause spectra to vary dramatically over very short distances which may correspond to only a few pixels. Thus, in some embodiments, it may be advantageous to undergo a second co-registration and training process. Thus, at block 1310, the digitally stained multiband data cube obtained in block 1308 may be co-registered with the stained multiband data cube to improve the alignment of features between the two data cubes. Co-registration is described in more detail below with respect to FIG. 14. At block 1312, the AI/ML model may undergo a second training to obtain a digitally stained multiband data cube.

The results of the training may be evaluated by, at block 1314, decompressing the digitally stained multiband data cube to obtain a digitally stained hyperspectral data cube. Decompressing the data cube can comprise generated spectrum from DCT coefficients using DCT basis functions. The system may, at block 1316, denormalize the digitally stained hyperspectral data cube and transform the data to an RGB representation. At block 1318, the system may transform the RGB representation to conform the image to an approved histopathological standard.

Figure 14:
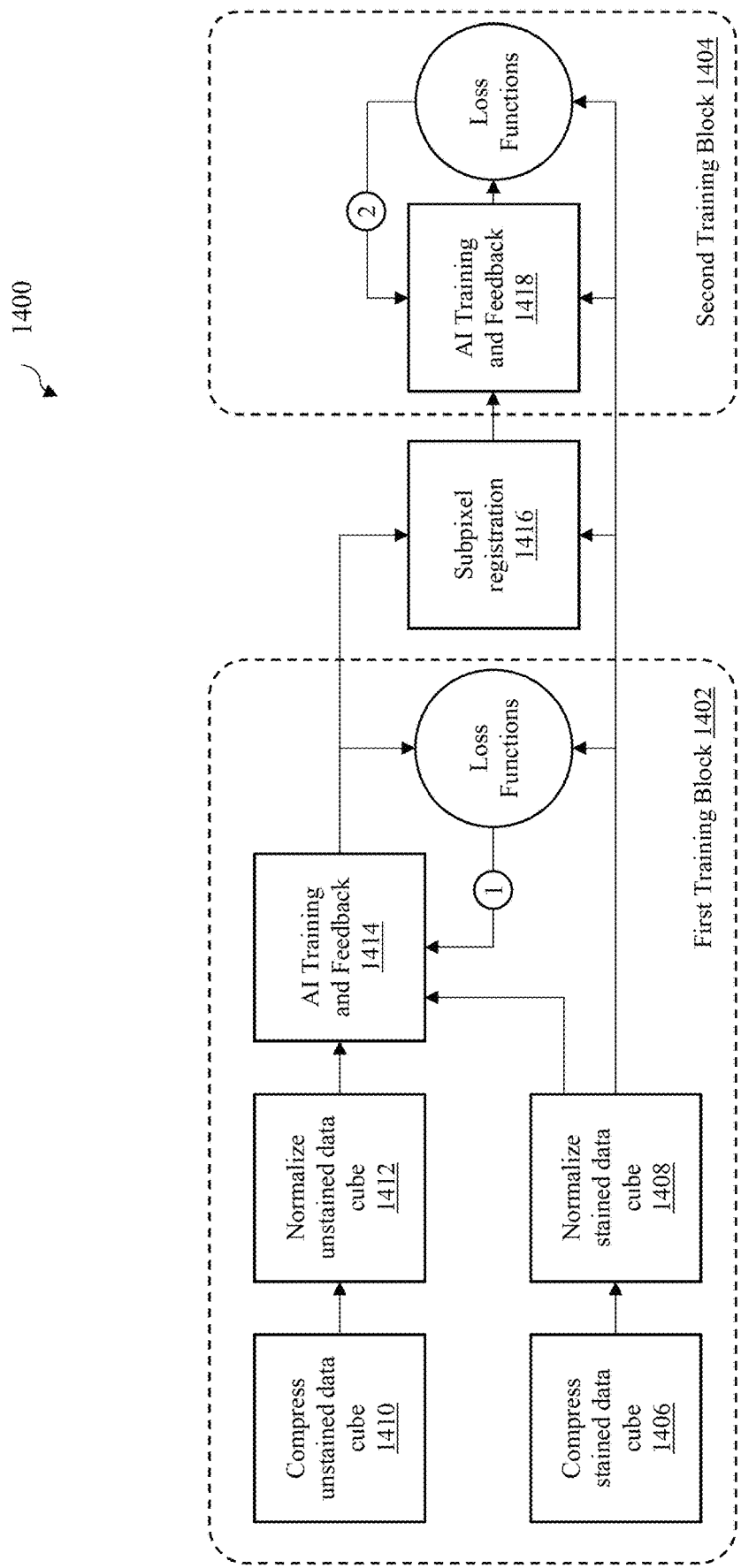
FIG. 14 is a block diagram illustrating an example of an artificial intelligence model training process according to some embodiments.

FIG. 14 illustrates an AI training process 1400 according to some embodiments. The AI training process 1400 may be run on a computing system. In a first training block 1402, a stained data cube may be compressed at block 1406 and normalized at block 1408. At block 1410, an unstained data cube may be compressed and, at block 1412, normalized. The compressed and normalized stained data cube and the compressed and normalized unstained data cube may be fed into a first AI model for training and feedback at block 1414. In some embodiments, AI training and feedback 1414 may utilize custom loss functions. At circle 1, model parameters may be adjusted using forward and/or backward propagation. The result of the first training block 1402 (e.g., a digitally stained, compressed, normalized data cube) may be used alongside the compressed, normalized stained data cube as inputs into a subpixel registration algorithm at block 1416. The subpixel registration block 1416 outputs may be fed into a second training block 1404 comprising a second AI training and feedback block 1418. At circle 2, the model parameters may be adjusted using forward and/or backward propagation. In some embodiments, the AI model at AI training and feedback block 1418 may be the same as the AI model at AI training and feedback block 1414. For example, the subpixel registration learned in step 1416 may be applied to re-register the normalized unstained data cube generated at step 1412 with the normalized stained data cube generated at step 1408), or there may be two different models. A similar training approach is explained in additional detail with reference to FIG. 24 below. In some embodiments, some or all features of the training process in FIG. 24 can be used.

In some embodiments, a training set may be collected by measuring preselected unstained tissue samples (for example, from frozen section or paraffin-embedded specimens) under a microscope. The samples may then be chemically stained using multiple chemical baths based on the required staining (for example, pink staining using eosin for the cellular and tissue background, and deep-blue purple staining using hematoxylin for cell nuclei). The stained and unstained tissue samples may then be co-registered to a high degree of accuracy. For example, the co-registration error may be less than 25 μm, less than 10 μm, or less than 1 μm. Preferably, the co-registration error may be less than about 1 μm (e.g., about 10% of the size of a single nucleus). In some embodiments, mechanical co-registration (e.g., alignment of the slide on the microscope) may be adequate. However, at times it may be advantageous to use algorithm-based automated registration software or to manually register the images using human-eye observation of tissue features. In some embodiments, fiducial markers may be introduced on the slide substrate or another location and used for co-registration. For example, fiducials can be etched or otherwise formed on the slide substrate in a manner that ensures the fiducials do not shift or get washed away during slide preparation steps.

In some embodiments, the stained and unstained images may be lamp-normalized. For example, the minimum and maximum intensities may be normalized between the unstained and stained images. In some embodiments, the normalization may be done for each wavelength as opposed to doing a single normalization that applies to all wavelengths. Lamp normalization may not always be performed. However, lamp normalization can be especially beneficial when stained and unstained images are captured lamps with different emission spectra. For example, a lamp's emission spectrum can change over time due to aging, changes in ambient temperature, the amount of time the lamp has been powered on, and so forth. In some embodiments, a different lamp may be used for the unstained and stained images, for example because a lamp bulb was replaced.

In some embodiments. multiband data cubes may be prepared from hyperspectral data by reducing the number of bands. Depending on the quality desired, a lossless or lossy compression algorithm may be used. Lossless compression results in an exact replica of the original image after decompression and reconstructions, while with lossy compression, redundant spectral and spatial components may be removed with some loss of information. Spatial redundancies may occur due to the similar intensity of neighboring pixels. Spectral redundancies may occur due to nearby pixels having similar spectra. There may also be temporal redundancies in hyperspectral image data. This may occur, for example, if the same area was scanned more than once. Compression may be done using a transform-based, prediction-based, learning-based, vector quantization-based, compressive sensing-based, tensor decomposition-based, sparse representation-based, or multi-temporal-based algorithm. In some embodiments, principal components analysis (PCA) or maximum noise fraction (MNF) transform may be used. In some embodiments, discrete cosine transforms may be used.

Figure 15:
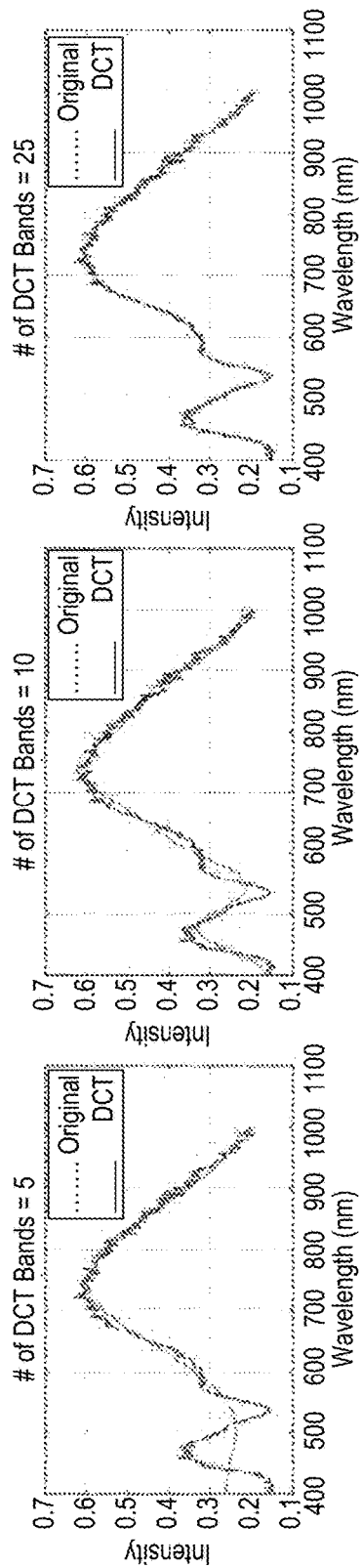
FIG. 15 illustrates an example of spectral waveforms with hyperspectral image compression according to some embodiments.

Compression may exploit the spatial relationships, spectral relationships, or both which may be present in the data. Thus, it is possible to reduce both spectral and spatial data. In some embodiments, it may be preferable to reduce the number of spectral bands without compressing spatial information. For example, because the composition (and the spectral properties) of a tissue sample can change rapidly, it may be important to preserve spatial information. In some embodiments, a discrete cosine transform may be applied to the spectral bands of each pixel. A system may apply a discrete cosine transform to, for example, compress a raw spectrum (which may have several hundred or more different wavelengths) using fewer than about 5, fewer than about 10, fewer than about 15, few than about 20, fewer than about 25, fewer than about 30, any number in between these numbers, or even more if desired basis functions. Each basis function can have an associated weight coefficient. The spectrum can then be represented by the weight coefficients of each basis function. The storage requirements can then be reduced by a factor of about N/L, where N is the number of basis functions and L is the number of data points in the spectrum. FIG. 15, for example, depicts discrete cosine transform fitting using 5, 10, and 25 basis functions. A greater number of basis functions may result in a better fit to the original data but can require corresponding greater storage and computing resources. In some embodiments, the mean squared error when using a discrete cosine transform may be greater than the mean squared error when using other techniques such as principal components analysis. However, in some embodiments, it may still be preferable to use a discrete cosine transform. Advantageously, a discrete cosine transform can use basis functions that are independent of the image, and fast computational algorithms are known. By applying discrete cosine transforms (or another appropriate transform) to each pixel in a hyperspectral data cube, the system may generate a multiband data cube comprising a tensor with a reduced number of bands.

A multiband data cube pair may be normalized to express the minimum and maximum intensity values according to a defined scale. For example, the minimum may be defined as 0 or −1, and the maximum may be defined as 1. Applying such a normalization to the multiband data cube pair may have many advantages for training an AI/ML model. For example, many AI/ML algorithms either prefer or require normalized input data. For example, linear regression algorithms, non-linear regression algorithms, logistic regression algorithms, k nearest neighbor algorithms, neural networks, clustering algorithms, and support vector machines may expect or require normalized input data.

Normalized data may be provided to an AI model for training to perform digital staining. The AI/ML model may be, for example, a conditional generative adversarial network (GAN). In a GAN framework, a generator model learns mapping from the training data cube to perform digital staining. A second, discriminator network may learn to discriminate between the generated image and a ground truth data cube (e.g., the physically stained data cube). These two networks may be trained at the same time and conditioned upon the stained data cube. This training may be a first training using a first registration-corrected data cube pair. During training, the system may use forward and backward propagation and may update the network parameters of the model during each iteration.

In some embodiments, a system may perform a second co-registration process using the results from the first training and the physically stained data cube. A multiband data cube pair (which may comprise, for example, a stained data cube and a digitally stained data cube) may be converted to an RGB image by performing decompression, denormalization, and color transformation steps. The system may then compare the images, for example by determining structural similarity index measure (SSIM) metrics. Other measures can also be used in addition or alternatively, such as mean square error (MSE), peak signal to noise ratio (PSNR), and feature similarity indexing method (F SIM). An SSIM index (e.g., quality assessment index) can be based on the various terms, such as luminance, contrast, and structure. The overall index can be a multiplicative combination of the terms. If the index is not within a threshold value, then the system may transform the pixels in the digitally stained RGB image by, for example, constructing a homography matrix for translating and/or rotating the image in small steps. In some embodiments, the system may also be configured to transform the digitally stained image by, for example, scaling the image based on a swelling or contraction of the tissue sample as a result of physical staining.

In some embodiments, additional training of a second AI model may be performed using the co-registered digitally stained multiband data cube. In some embodiments, the second model may be similar to the first model. For example, in some embodiments, the second model may be the same as the first model except for one or more parameter values. For example, both may use deep conditional generative adversarial networks. In some embodiments, rather than or in addition to training a second model, the co-registration information for the digitally stained multiband data cube may be applied to the unstained data cube and the first AI model may be retrained using the revised co-registered pair. It will be appreciated that multiple models may be used in a cascaded configuration both during training or during use, or single models may be used, or other configurations may be used.

Figure 16:
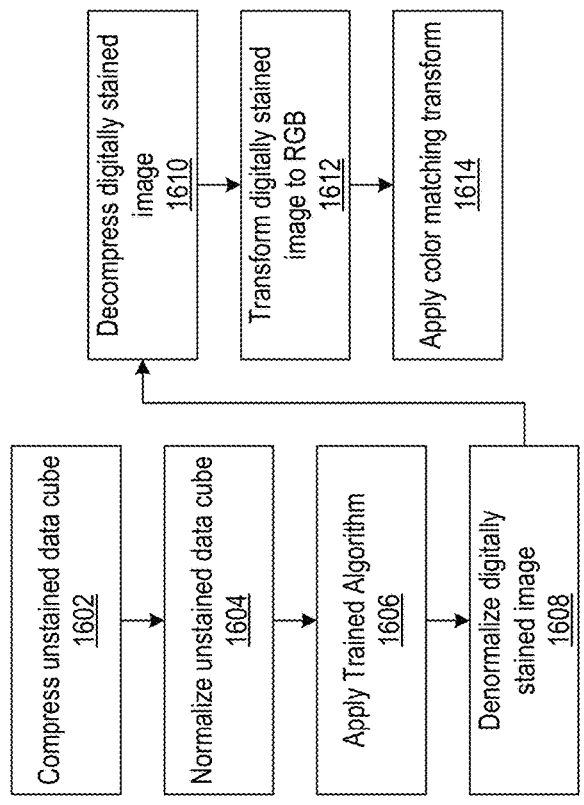
FIG. 16 is a block diagram illustrating an example process for performing digital staining according to some embodiments.

FIG. 16 illustrates a process 1600 for digital staining according to some embodiments. The process 1600 may be run on a computing system. At block 1602, raw hyperspectral data from an unstained tissue sample may be compressed to form a multiband data cube, for example by using a discrete cosine transform or another suitable compression algorithm. At block 1604, the multiband data may be prepared for input into a machine learning system, for example by normalizing the data. At block 1606, the system may apply a trained algorithm (for example, an algorithm trained according to FIG. 3) and may produce a digitally stained image. At block 1608, the system may denormalize the digitally stained image. At block 1610, the system may decompress the digitally stained image to form a hyperspectral digitally stained image, for example by performing an inverse discrete cosine transform or other suitable inverse transformation corresponding to the transformation that was used to compress the unstained hyperspectral data cube at block 1602. At block 1612, the hyperspectral data cube may be transformed into an RGB image or the like. At block 1614, one or more transformations may be applied to the RGB image. For example, in some embodiments, at block 1614, the colors, brightness, contrast, and so forth of the image may be adjusted so that the digitally stained image looks like a physically stained image.

In some embodiments, denormalizing and transforming a hyperspectral image to an RGB image has certain complexities. The conversion between hyperspectral data and RGB data may not be straightforward, especially when the hyperspectral data contains information from outside the visible range. Color matching functions may be applied to convert the hyperspectral data to RGB data, for example in the sRGB color space. In some embodiments, color matching functions may be provided by an external organization, such as the Commission Internationale de l'Eclairage. In some embodiments, the color matching functions may be stretched linearly or otherwise transformed so that they cover all of the wavelengths present in the hyperspectral data cube. In some embodiments, some wavelengths present in the hyperspectral data cube may not be considered when generating an RGB representation of the data.

In some cases, additional transformations may be applied to adjust the colors of the image. For example, an RGB image generated from hyperspectral data may deviate from "true" colors (e.g., what one would expect when performing physical staining) due to different processing steps, imaging conditions, operational inconsistency, imperfections in spectral matching algorithms, distortions from using stretched color matching functions, and so forth. In some embodiments, histogram normalization may be used to correct images. For example, a digitally stained image may be compared to an sRGB (or other color space) reference image of a chemical stain of interest by examining the histogram of the reference and the histogram of the digitally stained image. However, in some embodiments, matching a global histogram for a reference image to a global histogram for a digitally stained image may be problematic as there may be variations in the compositions between the images, colors may be incorrectly matched, and histological information may be lost.

Figure 17:
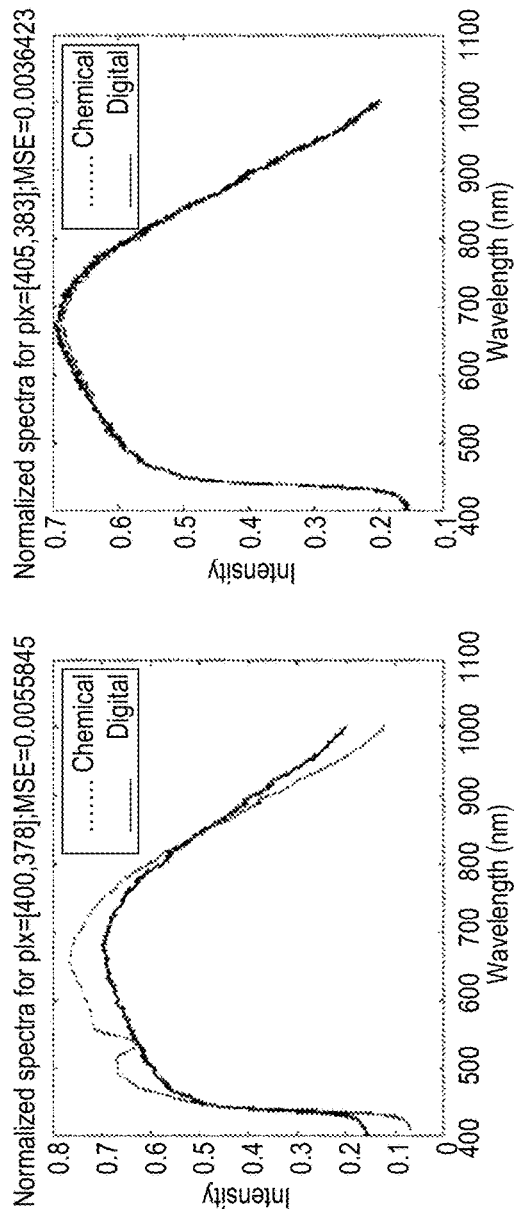
FIG. 17 illustrates a depiction of illuminant correction according to some embodiments.

To preserve histological information, a more complex color matching approach may be used. For example, the intensity of background or blank areas of histopathology images do not contain any stains. Thus, spectral variations in blank areas are associated with illuminant differences (e.g., differences in the emission spectrum of the lamps used for the reference and for the digitally stained images). Illuminant differences may be accounted for by, for example, applying a correction factor involving the ratio of the two background spectra. For example, if $V_{b,ref}$ is the spectral waveform of the background region of a reference image and $V_b$ is the spectral waveform of the background region of the digitally stained image, then a pixel of the digitally stained image may be corrected according to the relationship $V_{corrected} = (V_{b,ref}/V_b) V_{uncorrected}$, where $V_{corrected}$ is the corrected spectrum and $V_{uncorrected}$ is the uncorrected spectrum (e.g., the raw, as-captured waveform of the background region in the digitally stained image). It will be appreciated that this transformation may be applied to each wavelength of each pixel of the digitally stained image. FIG. 17 depicts an example spectrum without (left) and with (right) illuminant correction in comparison to a chemically stained image.

Absorption-Based Digital Staining

The embodiments described above are generally with reference to transmission spectra. However, it is not necessary to use transmission spectra. For example, absorption, reflection, or both can be used instead of or in addition to transmission. In some embodiments, it can be advantageous to use absorption spectra for performing digital staining or other processing of medical imaging or other spectral data. The transmission and absorption of light can be related to each other according to the Beer-Lambert-Bouguer law (hereinafter Beer's law). In particular, Beer's law defines the relationship between absorbed light and transmitted light as $A(\lambda) = -\ln(T(\lambda))$, where A is the absorption of the sample and T is the transmission through the sample. Both A and T depend on the wavelength $\lambda$. The absorption A is related to the thickness of the sample d and the absorption coefficient $\alpha(\lambda)$ by the relationship $A(\lambda) = \alpha(\lambda)d$. The relationship between absorption and transmission neglects any scattering of the light or deviations in absorption, refractive index, and so forth that may become significant under certain conditions. This relationship also neglects, for example, any non-uniformity of a glass slide or cover slip used in preparing a tissue sample slide. In some embodiments, absorption spectra determined from transmission data may be useful for digital staining despite these limitations.

Often, a sample may contain multiple absorbers. For example, in a tissue sample, there may be many different compounds present in varying concentrations throughout the sample. When there are N absorbers are present, the absorption A can be described as $A(\lambda) = \alpha_1(\lambda)d_1 + \alpha_2(\lambda)d_2 + \alpha_3(\lambda)d_3 + \ldots + \alpha_N(\lambda)d_N$. The absorption coefficient $\alpha(\lambda)$ can depend on the concentration of the absorber and the wavelength-dependent absorptivity coefficient (or extinction coefficient) of the absorber.

Figure 18:
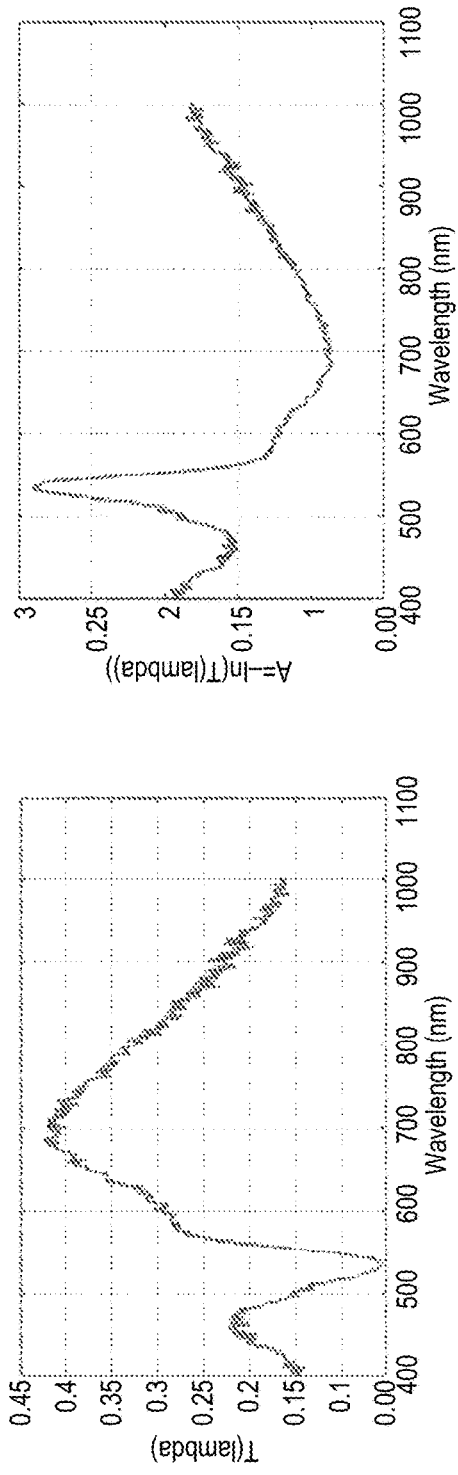
FIG. 18 depicts an example of transforming a transmission spectrum to an absorption spectrum according to some embodiments.

In some cases, it may be advantageous to convert collected transmission data into absorption data and to perform machine learning training or other analysis using the absorption data. An example of the transformation between transmission and absorption is shown in FIG. 18. Plot 1802 shows a transmission spectrum for a single pixel from a stained tissue sample. Plot 1804 shows the corresponding absorption spectrum for the same pixel.

Model Training

Figure 19:
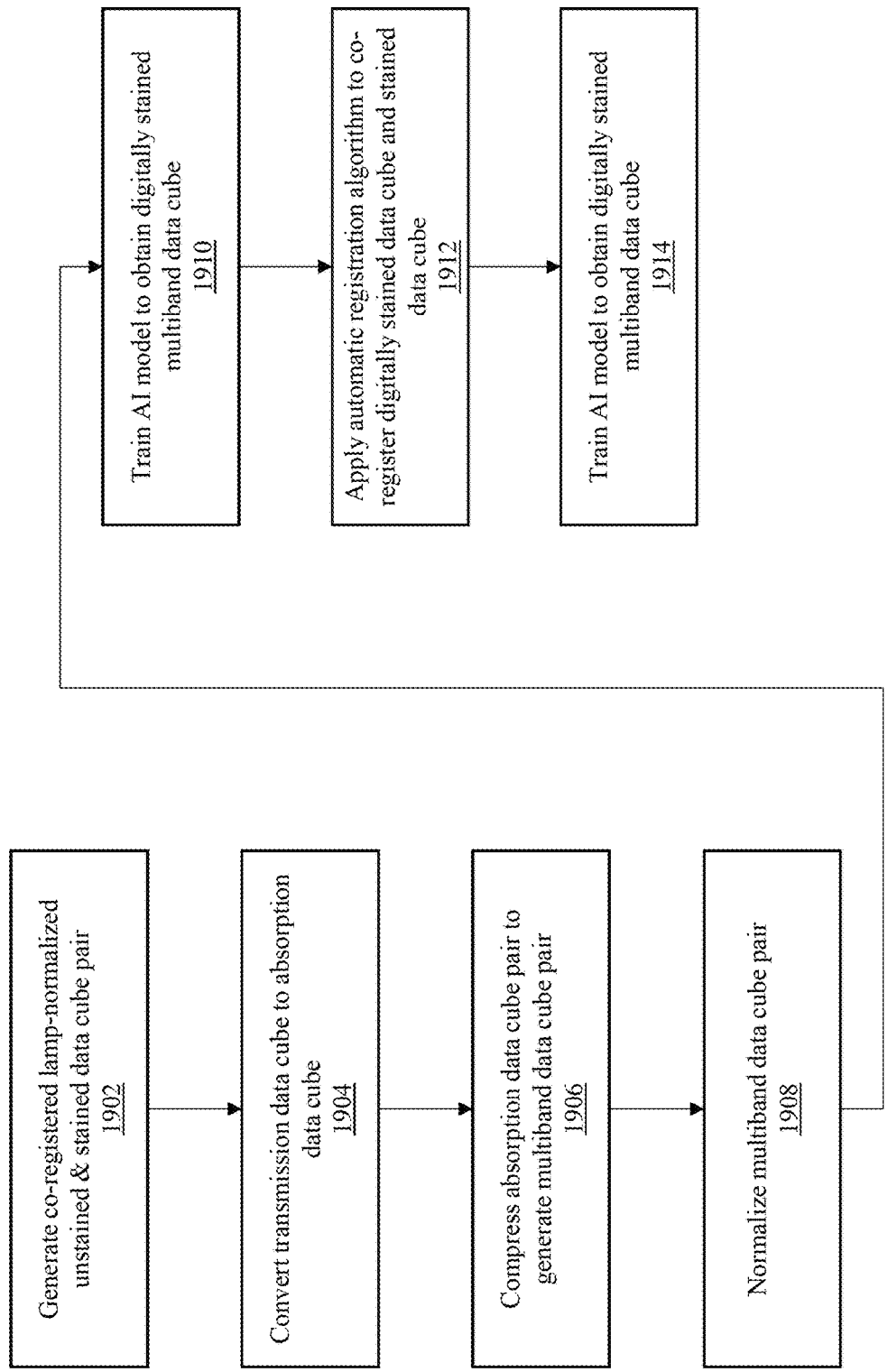
FIG. 19 depicts an example process according to some embodiments for training a machine learning (ML) or artificial intelligence (AI) model using absorption data.

FIG. 19 depicts an example process according to some embodiments for training a machine learning (ML) or artificial intelligence (AI) model using absorption data. The process may be run on a computing system. At block 1902, the system may generate a co-registered, lamp-normalized data cube pair from an unstained image and a stained image of the same tissue sample, which may contain transmission data. At block 1904, the system may convert the transmission data into absorption data to produce an absorption data cube pair. At block 1906, the system may optionally compress the absorption data cube pair to generate a multiband data cube with a reduced number of bands, for example by applying a discrete cosine transform or other suitable transformation. In some embodiments, the AI/ML model may be trained using raw data (for example, uncompressed hyperspectral data). However, in some embodiments, it may be advantageous to compress the data, for example in order to reduce computational demands.

At block 1908, the system may normalize the multi-band data cube pair in preparation for training an AI/ML model. For example, the system may scale values within the data cube pair so that a maximum value is 1 and a minimum value is 0 or −1. At block 1910, the system may perform a first pass training of an AI/ML model to obtain a digitally stained multiband data cube from an unstained multiband data cube. At block 1912, the system may perform an additional registration step. For example, the system may apply an automatic registration algorithm to co-register the digitally stained multiband data cube and the stained multiband data cube to further refine registration between the digitally stained data cube and the stained data cube. As described above, the co-registration can include translations, rotations, stretching, compressing, and so forth. In some embodiments, limitations can be imposed on the co-registration process, for example to limit the loss of active tissue field near a boundary that can occur when translations and/or rotations are relatively large. At block 1914, the system may perform a second pass training of the AI/ML model to refine the digitally stained multiband data cube. In some embodiments, a third pass, fourth pass, or more may be performed. In some embodiments, rather than a second pass training of the same model, a different model may be trained at block 1914.

In some embodiments, the registration at block 1912 can be performed using absorption data. For example, the output at block 1910, which can be a digitally stained absorption image, which can be co-registered with an absorption spectrum derived from the transmission data of a stained image, for example as produced at block 1904 and/or to the compressed absorption data produced at block 1906. For example, the digitally stained image can be compared to raw absorption data if the digitally stained image is decompressed or can be compared to compressed absorption data if the digitally stained image is compressed.

In some embodiments, the additional registration at block 1912 may comprise converting the digitally stained multiband absorption data cube to a transmission data cube. The system may decompress the digitally stained multiband transmission data cube, denormalize the digitally stained multiband transmission data cube, and transform the digitally stained multiband transmission data cube and the stained transmission data cube into respective RGB images (e.g., rather than have a spectrum associated with each pixel, each pixel can have red, green, and blue values). The RGB images may be compared using a structural similarity index measure (SSIM). SSIM may be used for measuring the similarity between digitally stained RGB images and chemically stained RGB images. If the structural similarity index is not within a threshold value, the system may transform the digitally stained RGB image by constructing a homography matrix for translating and rotating the digitally stained RGB image. Small translations and/or rotations of the digitally stained RGB image may be performed until a desired similarity index value is achieved, until the similarity index converges to a value (e.g., when additional iterations do not change the similarity index by more than a threshold amount), until a maximum number of iterations has been performed, and so forth. The corrections resulting from the registration at block 1912 may be used to co-register the digitally stained absorption multiband data cube with the stained multiband data absorption cube. Alternatively or additionally, the corrections resulting from the registration at block 1912 may be applied to the unstained absorption multiband data cube. In some embodiments, co-registration can be performed using only luminance or intensity data. In some embodiments, co-registration can be performed using data from all of the channels of the image.

The AI model trained at block 1910 and at block 1914 (which may be the same model or different models) may be deep conditional generative adversarial networks. In some embodiments, if multiple models are trained, then in use the multiple models may operate in a cascaded configuration. The process above has been described for a single data cube pair. However, it will be appreciated that the AI/ML training process may use a plurality of data cube pairs during the training process.

An AI/ML model can be trained using various methods. For example, an AI/ML model can be trained as described with reference to FIG. 3 above. In some embodiments, the AI/ML model can use paired stained and unstained images for training.

Model Deployment

Figure 20:
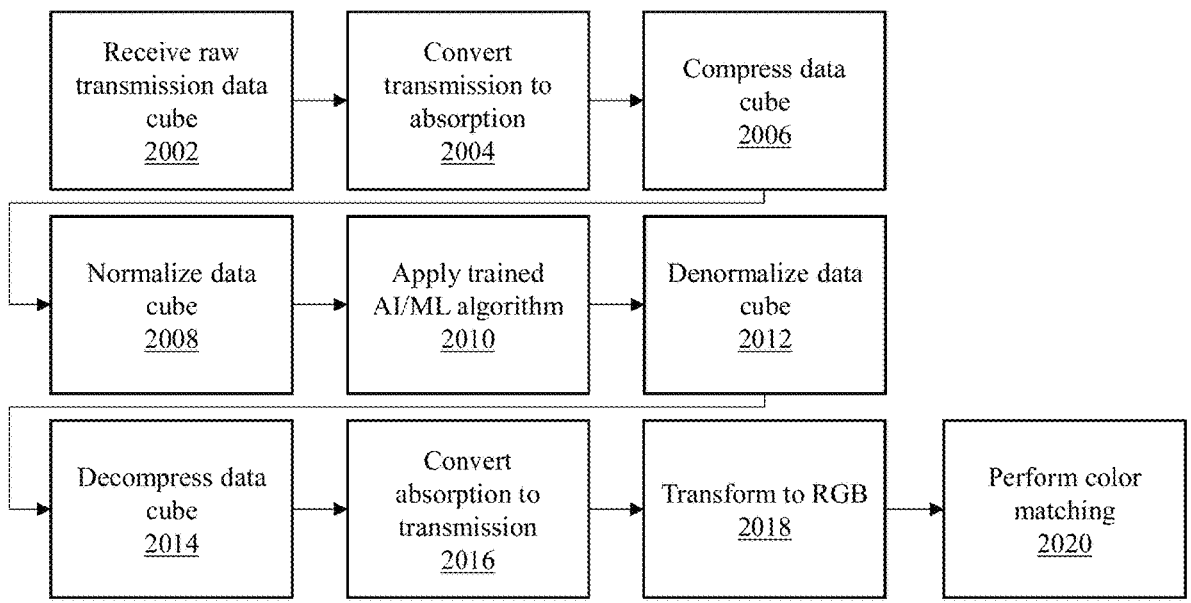
FIG. 20 depicts an example process for training an AI/ML model according to some embodiments.

FIG. 20 depicts an example process for digitally staining images according to some embodiments which may be implemented on a computing system. At block 2002, the system may receive a raw transmission data cube which may be, for example, a hyperspectral image, multispectral image, fluorescence image, and so forth. At block 2004, the system may convert the received raw transmission data cube to an absorption data cube. At block 2006, the system may compress the absorption data cube, for example by applying a discrete cosine transform or other transformation. At block 2008, the system may normalize the absorption data cube in preparation for applying a trained AI/ML algorithm at step 2010 to digitally stain the compressed absorption data cube. At block 2012, the system may denormalize the digitally stained absorption data cube. At block 2014, the system may decompress the compressed digitally stained absorption data cube. At block 2016, the system may convert the absorption data cube into a digitally stained transmission data cube. At block 2018, the system may transform the digitally stained transmission data to an RGB representation. At block 2020, the system may perform one or more color matching operations. For example, the system may match the colors in the digitally stained RGB image against a standard (e.g., a histopathologically approved standard or a reference RGB image) for a particular stain.

While the process shown in FIG. 20 is shown as converting a single, complete unstained data cube into a stained data cube, in some embodiments the process shown in FIG. 20 may be applied in real-time, in near real-time, or otherwise applied before an unstained data cube is fully captured. For example, a system may be connected to a microscope and configured to digitally stain an image during capture by, for example, digitally staining as each voxel is received, digitally staining as each line in an image is received, digitally staining after a group of lines is received (for example, performing digital staining after every fifth line, after every tenth line, and so forth). Use of the process in this manner may enable pathologists and others to make decisions before image capture is complete. For example, a pathologist might decide to apply a different digital stain, to prepare additional tissue sections, and so forth based on digitally stained partial images.

Multiplexed Staining

As discussed briefly above, in some cases it may be desirable for a pathologist to apply multiple stains to a tissue sample. With conventional chemical staining, this can require preparing multiple tissue samples. Digital staining allows multiple stains to be applied to a single tissue sample, and thereby may improve efficiency and may lead to improved diagnosis. In addition to this improved efficiency, digital staining can also enable imaging approaches that are difficult or impossible with chemical staining. Digital staining allows multiple stains to be applied simultaneously to the same image. That is, digital staining enables the creation of composite images with a mixture of multiple stain combinations in different regions. For example, within a single image, one region can have one digital stain applied, while another region can have another, different digital stain applied. Such multiplexed imaging can enable more accurate diagnosis.

Figure 21:
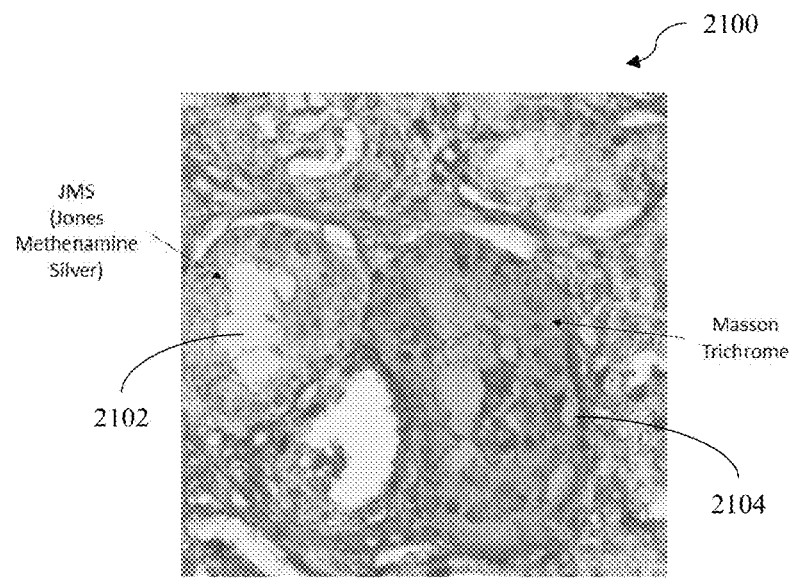
FIG. 21 illustrates an example multiplexed image according to some embodiments.

FIG. 21 shows an example multiplexed image 2100 according to some embodiments. In FIG. 21, a tissue field is shown with a hematoxylin and eosin (H&E) stain. A first region 2102 may be digitally stained with a different stain, such as Jones methenamine silver (JMS) and a second region 2104 may be stained with still another stain, such as Masson's trichrome (MT). The H&E stain may enable easy differentiation of cell nuclei and cytoplasm, while JMS can provide contrast to basement membranes, and MT can be used to differentiate between collagen and smooth muscle in tumors. By applying multiple stains simultaneously to different regions of the same image, a pathologist may better be able to make a diagnosis.

Figure 22:
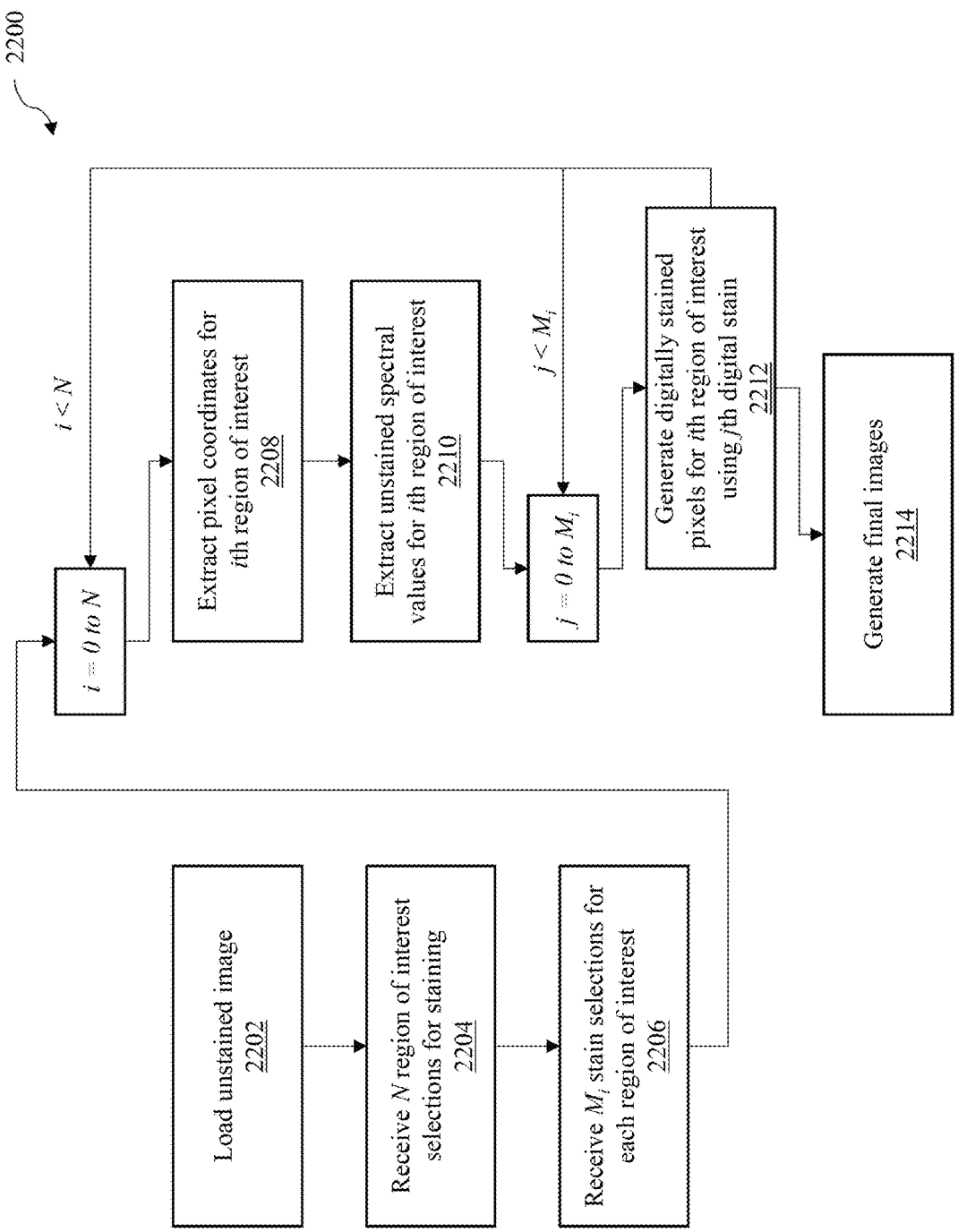
FIG. 22 is a block diagram depicting an example process for multiplexed digital staining according to some embodiments.

FIG. 22 is a block diagram that illustrates a process 2200 for multiplexed digital staining according to some embodiments. The process 2200 may be performed on, for example, a computing system such as a desktop, laptop, tablet, smartphone, or other suitable device. At block 2202, the system may load an unstained image which may be, for example, a hyperspectral image, multispectral image, and so forth. At block 2204, the system may receive a selection of one or more (N) regions of interest for digital staining. In some embodiments, a user may manually select regions for staining, for example by using an input device such as a mouse to draw an area for staining. In some embodiments, the system may automatically select regions. For example, the system may detect edges in an image or changes in the spectral data, which may allow the system to automatically detect regions or to aid a user in selecting regions. In some embodiments, a stain may be applied to any unselected regions. For example, the system may be configured to apply a hematoxylin and eosin stain to any regions that are not selected.

At block 2206, the system may receive one or more ($M_i$) stain selections for each of the N selected regions of interest. Different stains may be selected for different regions, or the same stain may be selected for different regions. In some embodiments, a user may select more than one stain for a selected region. At block 2208, the system may extract the pixel coordinates for the ith region of interest and, at block 2210, the system may extract the unstained spectral values for the ith region of interest. At block 2212, the system may apply the selected stains to the selected regions. The system may repeat block 2212 to apply $M_i$ different digital stains to the ith region of interest. The system may repeat blocks 2208, 2210, and 2212 for each ith region of interest of the N regions of interest. At block 2214, the digitally stained regions of interest and the unselected regions (which may be unstained or digitally stained) may be combined by the system to form a final composite image or images.

In some embodiments, the system may allow a user to visualize multiple stains for a single region of interest. For example, the system may present the user with an interface that allows the user to select a region in the final composite image and select different digital stains that were applied to the region. For example, a pathologist may click, flip, scroll, or otherwise browse through multiple stains for a particular region of interest and select a stain that best provides diagnostic information, which may lead to improved diagnosis, may reduce analysis time, and so forth.

Digital Staining Using RGB Image Data

Some embodiments herein describe systems and methods for processing complex medical imaging and spectroscopy data. Such methods can, in some embodiments, be used for less complex data, such as RGB images. However, it can be beneficial to provide systems and methods that are optimized for dealing with particular types of data. For example, an RGB image may contain only three channels (e.g., red, green, and blue channels), while a hyperspectral or multispectral image may contain many channels. There can be many advantages to working with RGB images instead of or in addition to hyperspectral or multispectral images. For example, not all practitioners may have access to the specialized equipment used for capturing hyperspectral or multispectral images. Capturing complex imaging data can be time-consuming in comparison to capturing RGB microscopy images, as complex imaging data is often captured by collecting information in different wavelength ranges at different times.

The use of RGB images can alleviate some problems associated with other forms of imaging because equipment that may not be readily accessible to a practitioner is not needed and images can be captured quickly using common microscopy equipment. Additionally, the use of RGB images can simplify image processing steps that are performed as part of digital staining processes. For example, RGB images can be relatively small compared to hyperspectral or multispectral images, and an RGB image can comprise only three channels, rather than tens, hundreds, or even thousands of channels. Accordingly, there may not be a need to compress or downsample images to obtain acceptable performance of a digital staining system, to conserve storage space, and so forth.

In some cases, digital staining can be performed using only a limited number of channels from a hyperspectral or multispectral image. For example, digital staining can be performed using ten channels, five channels, or three channels. The skilled artisan will appreciate that while the number of channels can be reduced, the particular channels (e.g., wavelength ranges) generally cannot be arbitrarily selected, as there needs to be sufficient information (e.g., transmission peaks/troughs) from which a digital staining model can work. The number and location on the electromagnetic spectrum (e.g., wavelength ranges) of channels can depend on the particular digital stain to be applied. For some stains, there can be sufficient information available in the visible spectrum such that an RGB camera can be used to capture images. For hematoxylin and eosin, for example, information in the visible region of the electromagnetic spectrum can provide sufficient information to enable accurate digital staining. Other digital stains, whether based on physical or chemical stains or having no physical-world analog, can be applied to RGB images.

In some embodiments, a color camera that uses a charge-coupled device sensor or a complementary metal oxide semiconductor sensor can be used to capture an image suitable for use in digital staining. The sensor can be divided into a number of pixels and/or sub-pixels. A Bayer filter can be used to select a range of wavelengths to be captured by each subpixel. For example, a Bayer filter can comprise an array of red, green, and blue filters. The filters can allow red light, green light, or blue light to pass through the filter onto the sensor, while blocking other light. Advantageously, such an approach enables the simultaneous capture of all three channels (red, green, and blue, thereby reducing capture times. In some embodiments, the RGB camera can be configured to capture an entire tissue sample image simultaneously (e.g., as opposed to using a scanning process). For example, the camera can have a lens and aperture configured to receive light from an entire area of interest at once and to project the light on the sensor. In some embodiments, there can be less distortion of an image when using an RGB camera, as capture times can be reduced, thereby limiting the impact of any vibrations that may result in image distortion. Additionally, hyperspectral and multispectral imaging systems often have moving parts (for example, to change filters), the vibrations of which can result in image distortion.

In some embodiments, a camera could be a hyperspectral or multispectral camera providing only RGB output. In such a camera, red, green, and blue channels can be constructed by combining several hyperspectral bands with suitable red, green, and blue filters. In some embodiments the output of a hyperspectral camera or other camera can be standard RGB values or values in another well-known three-color space such as XYZ, LUV, LCh, L*a*b*, YCbCr, YUV, CMY. Such color spaces can be obtained by applying suitable transforms. An example of converting between RGB and YCbCr is described below.

While the discussion below refers to RGB image data, it will be appreciated that the systems and methods herein can be readily adapted to other three parameter color space (e.g., XYZ, LUV, LCh, L*a*b, YCbCr, YUV, CMY). The systems and methods herein can also be adapted to four parameter color spaces, such as CMYK, RGBD (where D represents a fourth channel or parameter), or any other arbitrary ABCD color space.

An artificial intelligence or machine learning (AI/ML) model can be trained to digitally stain unstained RGB images of tissue samples. In some embodiments, a single-stage model can be used. In some embodiments, however, a multistage model can be beneficial for digital staining. As briefly mentioned above and as described in more detail below, tissue sample images can contain densely packed features (e.g., cells, cell nuclei, lipids, extracellular matrix, cytoplasm, and so forth). Thus, it is important that even small features that may span only a few pixels to about 100 pixels are accurately represented in the digitally stained image. This can be challenging when using a single-stage model, as such a model may be tuned to recognize low frequency features (e.g., gradual transitions in color or luminance) but may not be tuned to recognize high frequency features such as the edges of nuclei. Conversely, a model can be tuned to recognize high frequency features but may perform relatively poorly in identifying low frequency features. Thus, in some embodiments, it can be advantageous to use a multi-stage model. For example, a first stage can be tuned to identify low frequency features and a second stage can be tuned to identify high frequency features. In some embodiments, the first stage can be tuned to identify high frequency features, and the second stage can be tuned to identify low frequency features. In such a configuration, the second stage can, in some embodiments, benefit from the identification of edges and other features by the first stage. In some embodiments, a GAN network can be used, as described briefly above. For example, the generative portion of the network can digitally stain the unstained image, and the adversarial portion of the network can attempt to discriminate between stained and digitally stained images. Ideally, the adversarial network should be unable to accurately guess which image is digitally stained. For example, the correct guess rate should preferably be as close to random chance as possible (e.g., as close to 50% as possible).

As mentioned above, features in a tissue sample image can be small as compared to the overall size of the image. For example, a cell nucleus, in some cases, may only be tens of pixels to about 100 pixels across. In training an AI/ML model, image pairs of stained and unstained tissue can be used as training data. For example, a tissue slide can be prepared, and an image can be taken of the unstained tissue using an RGB camera. The tissue can then be stained (e.g., stained with H&E or Trichrome, or with a specialized stained such as high molecular weight keratin (HMWK), Grocott's methenamine silver (GMS), and so forth) and imaged again using the RGB camera. These two images can form an image pair, and the AI/ML model's goal can be to manipulate the unstained image so that it closely resembles the stained image. If the images are not properly aligned with each other (co-registered), training can fail, resulting in a model that does not accurately perform digital staining of new unstained images that were not used during training.

The registration problem can be partially alleviated by, for example, aligning an edge of the tissue sample. However, changes to the tissue sample resulting from the staining process can make co-registration difficult. For example, some areas of the tissue sample can expand as a result of staining, while other areas can contract. Accordingly, in some embodiments, the stained image, the unstained image, or both can be translated, rotated, scaled, or otherwise deformed to co-register the images. In some embodiments, deformation can be uniform across the image. However, in some embodiments, a registration adjustment can vary throughout the image. For example, some areas can be made smaller while other areas may be made larger, for example to account for elastic deformation resulting from a staining process. For example, within a tissue sample, some regions may expand as a result of staining, while others may contract.

As described in more detail below, in some embodiments, generating an AI/ML model can comprise multiple registration and training steps. For example, after performing digital staining, co-registration can be performed between the digitally stained image and the stained image, and the model can undergo additional training.

Figure 23:
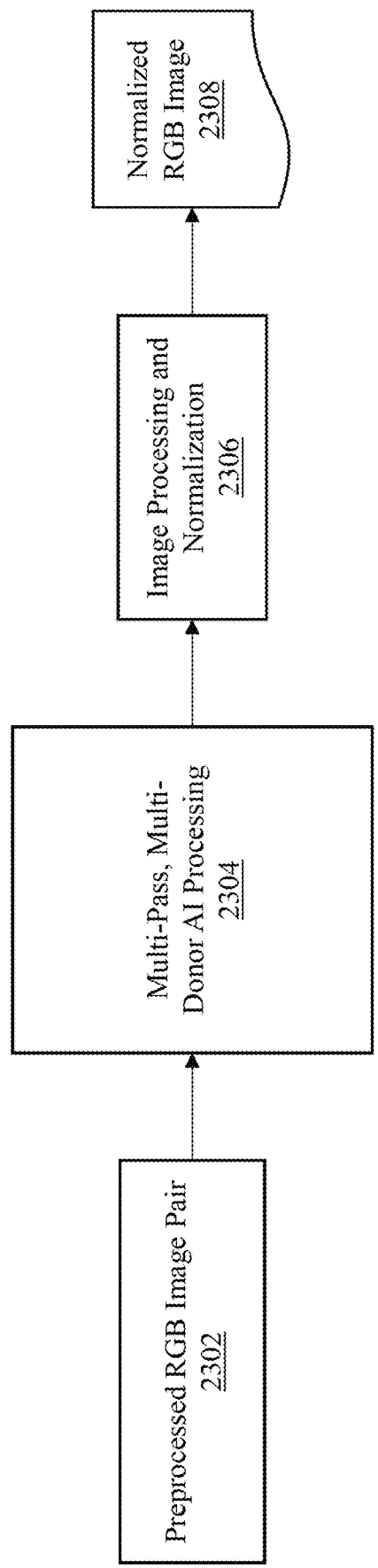
FIG. 23 illustrates an example process for training and deploying a model for digitally staining RGB images according to some embodiments.

FIG. 23 illustrates an example process for training and generating. A preprocessed RGB image pair 2302 can undergo multi-pass, multi-donor AI processing at block 2304. The output of the multi-pass, multi-donor AI processing can be a digitally stained image. At block 2306, image processing such as normalization and color correction can be performed, resulting in normalized RGB image 2308, which can be, for example, a digitally stained image. The various steps illustrated in FIG. 23 will be explained in more detail below.

In preparing an image pair for processing (e.g., an unstained and stained image of the same tissue), the image pair can be co-registered to ensure that features in the unstained image match up with features in the stained image. Registration can be especially important because, as discussed above, the features in a tissue sample slide, for example, can be very small. For example, without a registration step, typically errors can be in the range of about 100 pixels. A cell nucleus can have a size of about 100 pixels, depending on the magnification at which the image is captured by the microscope. Thus, a typical registration error can encompass a significant portion (in some cases, substantially all) of a feature in an image. In some embodiments, a system can be configured to perform registration by, for example, locating one or more fiducials present on a microscope slide. While a single preprocessed image pair is shown in FIG. 23, it will be appreciated that in practice multiple images can be provided to an AI/ML model. In some embodiments, image pairs from multiple donors can be provided to the AI model. Providing training images from multiple donors can be important because, for example, while similar tissue (e.g., liver tissue) can be similar between donors, there can be some variation, some of which may be unexplained and some of which may be due to a variety of donor factors such as gender, age, race, and so forth. By training the AI/ML model using images from a variety of donors, the AI/ML model can be made more generally applicable.

FIG. 23 illustrates the use of a multi-pass algorithm. While such an approach that includes multiple passes and/or multiple registration steps can be beneficial, in some embodiments, single-pass AI/ML training can be used. For example, if the input training image pairs are well-registered, single-pass training may be used to produce suitable digital staining results.

As shown in FIG. 23, after generating an image, the resulting digitally stained image can undergo postprocessing, as described in more detail below. This can be important because, for example, while the AI/ML model may produce a digitally stained image of sufficiently high quality in terms of accurately representing features, there can be discrepancies in the color of the digitally stained image as compared to a chemically or physically stained image. For example, a shade of pink may be too light or too dark, colors may appear washed out, and so forth. This can make interpretation of the digitally stained image difficult, as practitioners are accustomed to viewing chemically or physically stained tissue and thus may expect particular colors when viewing digitally stained images.

Model Structure and Training

In some embodiments, an AI/ML model (also referred to herein as a digital staining model) can comprise a convolutional neural network (CNN). In some embodiments, the CNN can comprise a plurality of neurons. In some embodiments, each neuron can be responsible for a local receptive field comprising a defined region of an image. A receptive field can be a defined portion of the image, for example defined by a filter size of a layer within a CNN. The receptive field can indicate a selection of input data that a neuron (or other unit within a CNN layer) is exposed to. In some embodiments, the AI/ML model can comprise multiple layers. In some embodiments, early layers in the CNN network (e.g., the first layer in a CNN) can be associated with relatively small receptive fields. This approach can help to enable learning features such as lines, edges, and other details that make up an image. In some embodiments, higher layers in the CNN can be exposed to larger receptive fields as the small receptive fields in lower layers combine to form larger receptive fields.

In some embodiments, a single layer, multilayer, and or multi-stage AI/ML network can be used to monitor the training process. For example, the AI/ML network can compare features of generated digitally stained images with features of chemically stained images. The compared features can be used to further adjust the weights in a digital staining model.

In some embodiments, an image can be divided into a plurality of fields. For example, an image can be divided into subfields comprises a number of pixels. Larger subfields can provide improved results, but may require more computing resources than if smaller fields are used. Advantageously, if an image is divided into the subfields, there can be overlap between the subfields. For example, a first subfield and second subfield may both contain some pixels of the full image, while each can also contain pixels that are not included in the other. This approach can, in some embodiments, improve the performance and/or training speed of an AI/ML model. For example, it can be beneficial to train the model on a mix of information that it has previously seen and new information. In some embodiments, a subfield can be square. For example, a subfield can be 16×16 pixels, 32×32 pixels, 64×64 pixels, 96×96 pixels, 128×128 pixels, 256×256 pixels, 512×512 pixels, and so forth. In some embodiments, a subfield may not be square.

In some embodiments, the CNN can comprise multiple stages. In some embodiments, each stage can comprise one or more layers. In some embodiments, a first stage can be trained to detect relatively low-density structures. In some applications, a single stage can be suitable for image processing. For example, an image of a park may feature a green lawn, a blue sky, and some trees. The color of the sky, lawn, trees, and so forth may change somewhat throughout the image, but such changes are likely to be relatively slow and smooth. For example, the color of the sky may vary from a darker blue to a lighter blue, but it is unlikely to change rapidly from one color to another. In contrast, medical images of tissue samples, for example, often vary dramatically over even a few pixels due to the cellular nature of the tissue. A single stage may identify the general structure of the medical image but may fail to recognize enough structural details to enable a convincing, accurate digitally stained image to be produced.

As described above, in some embodiments, an AI/ML model may comprise, for example, a conditional generative adversarial network (GAN). In a GAN framework, a generator model learns mapping from the training data cube to perform digital staining. A second, discriminator network may learn to discriminate between the generated image and a ground truth data cube (e.g., the physically stained RGB image). These two networks may be trained at the same time. This training may be a first training using a first co-registered data cube pair. During training, the system may use forward and/or backward propagation and may update the network parameters of the model during each iteration.

Figure 24:
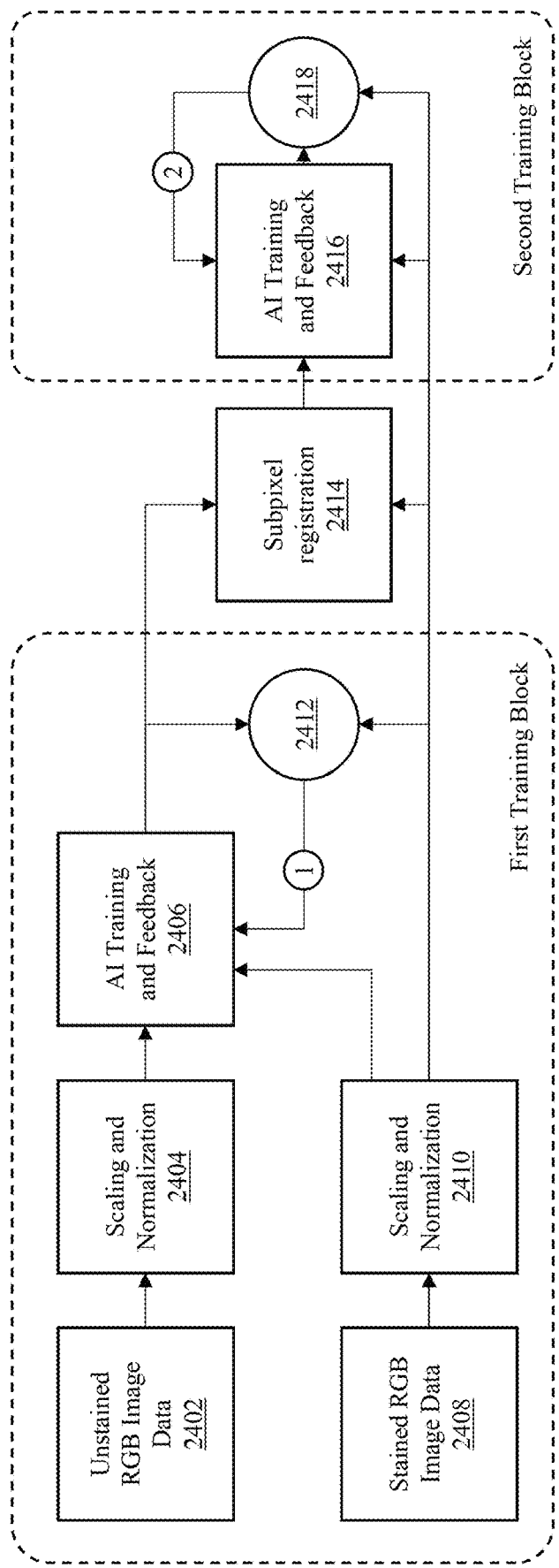
FIG. 24 illustrates an example process for training a model for digitally staining RGB images according to some embodiments.

FIG. 24 is a diagram that illustrates an example embodiment for training an AI/ML model to digitally stain RGB images according to some embodiments. Reference is made below to image pairs. It will be appreciated that training the model can involve the use of many images of stained and unstained tissue samples. Accordingly, the description below is not limited to training using a single stained tissue image and a corresponding unstained tissue image. A training data set can be created as described above, by imaging a collection of unstained tissue samples, staining the samples, then imaging the samples again. The stained and unstained images can then be co-registered using manual human alignment and/or algorithm-based automated registration as described above. In some embodiments, the stained and unstained images may be lamp-normalized as described above. However, such lamp normalization may not be included in some embodiments.

The training can be performed on a computer system. As shown in FIG. 24, at block 2404, the system can scale and normalize an unstained RGB image 2402. At block 2410, the system can scale and normalize a stained RGB image 2408. Together, the scaled and normalized input unstained image and the scaled and normalized input stained image can be a co-registered image pair. In some embodiments, the scaling and normalizing can include applying a denoising operation to the stained or unstained image. The scaled and normalized unstained RGB image 2402 can be digitally stained by the system at block 2406. After digital staining at block 2406, the system can compare the output of block 2406 (e.g., a digitally stained image) with the scaled and normalized stained RGB image. At block 2412, the system can compute loss functions. As described herein, loss functions can consider both local and spatial information in some embodiments. Using spatial information to compute the loss functions can help to reduce the likelihood that the training process reaches a local, rather than global, minimum. For example, loss functions can include L1 loss (e.g., absolute value of the prediction (e.g., digitally stained image pixel intensities and/or features obtained from various layers/stages in the AI/ML model) as compared to the ground truth (e.g., physically or chemically stained image pixels intensities and/or features obtained from various layers/stages in the AI/ML model)) and/or L2 loss (e.g., the square of the difference between the prediction and the ground truth). As described in more detail below, the training data can be divided into a plurality of subfields. There can be many subfields in a training data set. For example, there can be tens, hundreds, thousands, or millions of subfields. In some embodiments, loss functions can be computed using a subset of the unstained image data and the digitally stained image data. The output of the loss functions at block 2412 can be processed at circle 1 and used to adjust one or more weights of the model 2406. Training can continue using the input co-registered images, and loss functions can again be computed at block 2412. With each iteration, the loss functions can be computed using the same subfields or, advantageously, using a different set of subfields. The process can continue to find a minimum for the loss functions. Using this feedback mechanism, the training can continue until the loss function outputs indicate that the difference between the digitally stained image and the unstained image is within a threshold amount. As described herein, the AI/ML model can be trained using forward and/or backward propagation.

After exiting the first training loop, a second registration process can be performed at block 2414. In some embodiments, the second registration process can compare the digitally stained image to the stained image. In some embodiments, this comparison can be used to adjust one or more of the unstained and stained images (e.g., using one or more of translation, rotation, distortion, deformation, or scaling). The output of the subpixel registration at block 2414 can be an updated co-registered image pair created from the unstained RGB image data and the stained RGB image data. The adjusting can be performed as described elsewhere in this application, for example using single-stage and/or multi-stage structural similarity index measure metrics. In some embodiments, a structural similarity index measure can improve by from about 0% to about 25% or more, for example about 8%. In some embodiments, a translation error can be from about 0 pixels to about 20 pixels or more, for example from about 2 pixels to about 5 pixels. In some embodiments, a rotation error can be from about 0 pixels to about 10 pixels or more. In some embodiments, an expansion/contraction error can be from about 0 pixels to about 10 pixels or more, for example from about 1 pixel to about five pixels. The training process can then enter a second training loop. At block 2416, a system can perform a second training process using the updated co-registered pair generated at block 2414. The system can perform additional training of the model that was trained at block 2406 or may train a model with a different AI/ML network architecture. At block 2418, loss functions can be computed by comparing the output of block 2416 (e.g., a digitally stained image) to stained image data (e.g., the scaled/deformed and normalized stained RGB image, which in some embodiments may have had one or more transformations applied to it, for example depending upon which stained or unstained image pair was used for subpixel registration at block 2414). The output of the loss functions can, at circle 2, be used to adjust one or more model weights. The training process can operate as described above, considering portions of the stained and digitally stained image data. The training process can continue until the output of the loss functions is within a threshold range, which may be the same as or different than the threshold for exiting the first training loop.

While FIG. 24 illustrates a first and second training loop, it will be appreciated that additional loops can be used. For example, after minimizing the loss function in the second training loop, a third co-registered pair can be created and used in a third training loop.

As described above, a single model can be generated that accepts as an input an unstained image and that generates as an output a digitally stained image. However, in some implementations, rather than using stained and unstained image pairs for all training steps, a training process can use digitally stained images and stained images for some steps. For example, the second training loop of FIG. 24 could, instead of using stained and unstained image data for training, use stained and digitally stained image data. Such an approach can result in a cascaded composite model comprising a plurality of models, where each model operates at least in part on the output of the previous model in the cascade.

The preceding description discusses the use of a model for staining RGB images. However, it will be appreciated that any three- or four-parameter color space can be used. The above description can also be readily adapted to other forms of imaging or spectroscopy data, such as hyperspectral imaging data or multispectral imaging.

Color Correction

As discussed above while the AI/ML model may produce a digitally stained image of sufficiently high quality in terms of accurately representing features, but the colors of the image can be different from those of a conventionally stained tissue image, which can make interpretation challenging. Thus, in some embodiments, a color correction process can be applied to a digitally stained image so that the digitally stained image has colors that match what would be expected had a conventional staining process been used.

Figure 25:
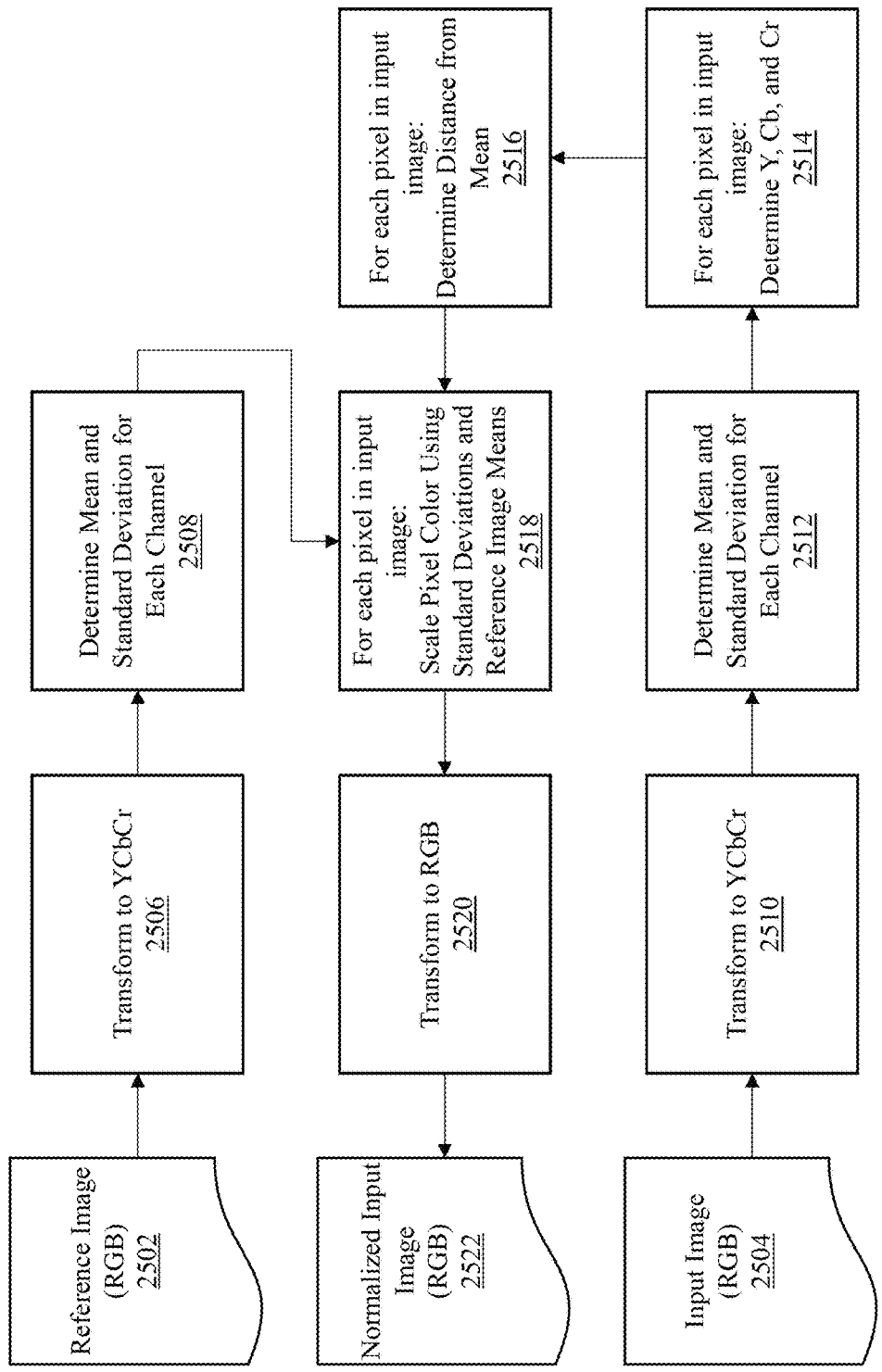
FIG. 25 illustrates an example process for color normalization according to some embodiments.

FIG. 25 illustrates an example process for correcting color of a digitally stained image according to some embodiments. A reference RGB image 2502 can be used as a basis for adjusting the input RGB image 2504. At block 2506, a system can convert the reference RGB image 2502 to a YCbCr image. At block 2508, the system can determine the mean and standard deviation for each channel of the YCbCr image (e.g., the mean and standard deviation of Y, the mean and standard deviation of Cb, and the mean and standard deviation of Cr). At block 2510, the system can convert the input RGB image 2504 to a YCbCr image. At block 2512, the system can determine the mean and standard deviation of each channel of the YCbCr input image (e.g., the standard deviations of Y, Cb, and Cr). At block 2514, the system can determine the Y, Cb, and Cr values for each pixel in the input YCbCr image. At block 2516, the system can determine the distance of each channel of each pixel from the mean for that channel (e.g., pixel (5,7) can have a Y standard deviation of 0.3 from the mean for the Y channel, a Cb deviation of −0.1 from the mean for the Cb channel, and a standard deviation of 1.2 from the mean for the Cr channel). At block 2518, the system can scale the values of each channel of each pixel of the YCbCr input image using the mean and standard deviation of each channel of the reference YCbCr image, resulting in a normalized YCbCr input image. The normalized YCbCr input image can then be transformed at block 2520 to RGB, resulting in normalized RGB image 2522.

A reference image can preferably be of the same tissue type as the input image. However, according to some embodiments, the reference image need not be of the same tissue type. The reference image can be an image of a conventionally stained tissue sample that has been stained using the same stain that is being digitally applied to the input image. For example, when applying an H&E digital stain, the reference image can be an image of a tissue sample that has been stained with H&E.

There can be several ways to scale an input image according to a reference image. In some embodiments, color correction can be performed using RGB data. However, in some embodiments, it may be advantageous to perform corrections in another color space that separates out intensity information from color information (e.g., HSV, HSL, YCbCr, etc.). According to some embodiments, an input RGB image and reference can be converted to YCbCr using the relations $$Y = \frac{1}{4}(R + 2G + B); Cr = R - G; Cb = B - G.$$

The YCbCr values of the input image can then be scaled according to the relation $T(x, t) = \bar{t} + (x - \bar{x})\, \sigma_t/\sigma_x$, where x is the value of the YCbCr representation of the input image, t is the value of the YCbCr representation of the reference image, and σ represents the standard deviation. x can be the Y, Cb, or Cr values taken from the YCbCr representation of the input image. t can be the Y, Cb, or Cr values taken from the YCbCr representation of the reference image. Application of the scaling relation can transform the input Y, Cb, and Cr values of the YCbCr representation of the input image to scaled values $Y_{out}$, $Cb_{out}$, and $Cr_{out}$. A normalized RGB image can then be produced via the relations $$G = Y_{out} - \frac{1}{4}(Cb_{out} + Cr_{out}); R = G + Cr_{out}; B = G + Cb_{out}.$$

Figure 26:
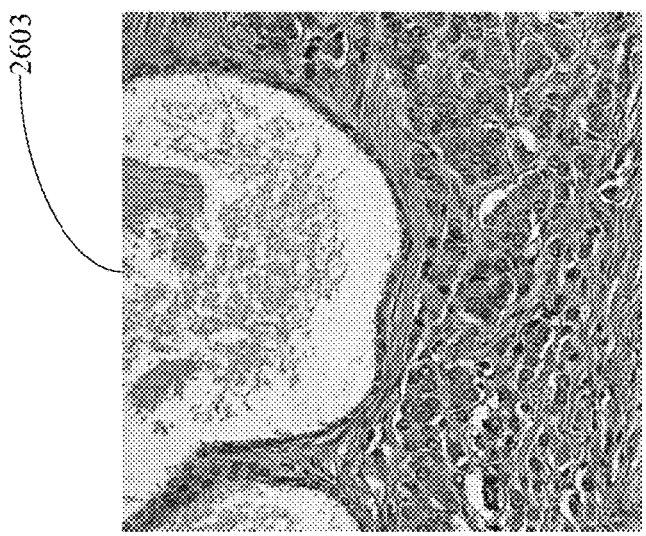
FIG. 26 illustrates an example of digital staining color adjustment according to some embodiments.
Figure 26:
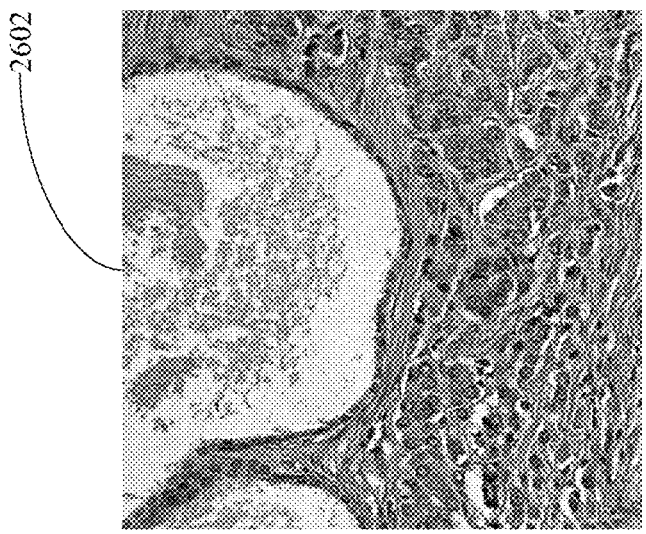
Figure 26:
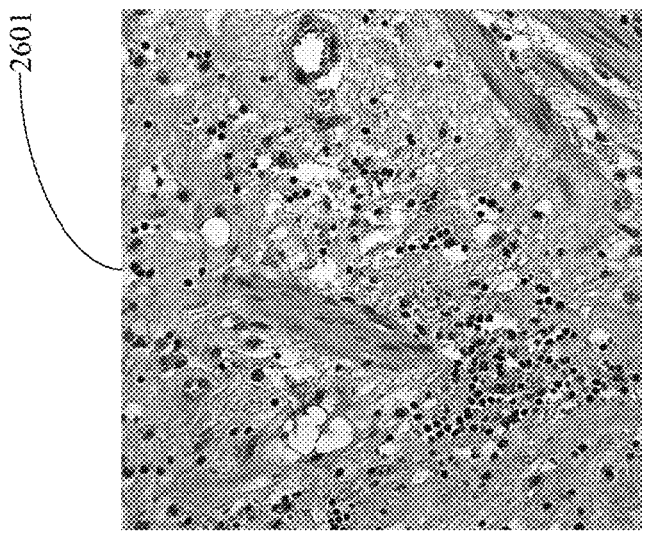

FIG. 26 shows an example of a color-corrected image according to some embodiments. A color-corrected image 2603 can be produced using digitally stained image 2602 and reference image 2601. As can be seen in FIG. 26, the colors of the digitally stained image 2602 can appear quite different from the colors of the reference image 2601, while after the color correction process, the reference image 2601 and color-corrected image 2603 can have very similar colorization.

Computer Systems

Figure 27:
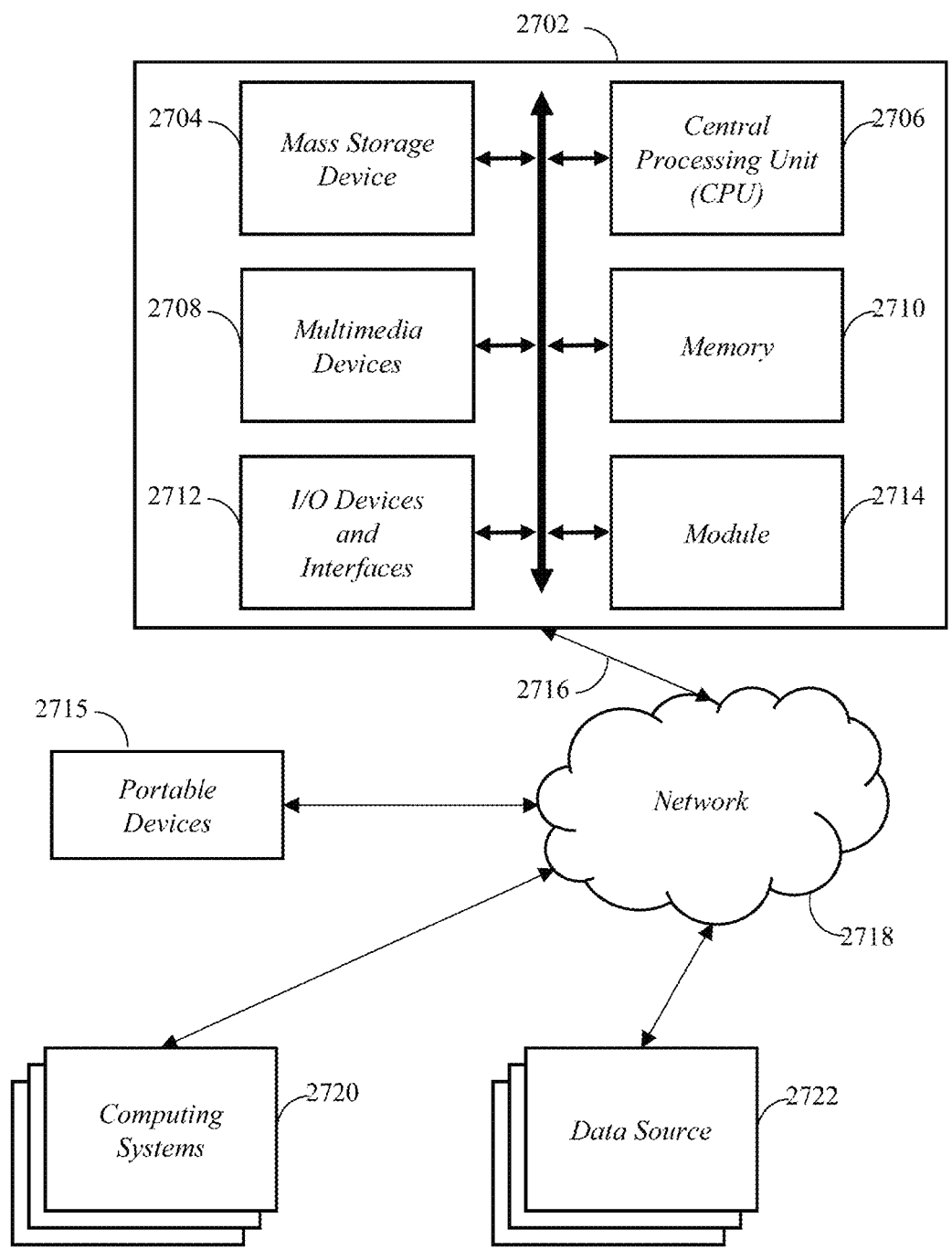
FIG. 27 illustrates an example computer system that can be used to carry out one or more embodiments described herein.

FIG. 27 is a block diagram depicting an embodiment of a computer hardware system configured to run software for implementing one or more embodiments of the health testing and diagnostic systems, methods, and devices disclosed herein.

In some embodiments, the systems, processes, and methods described herein are implemented using a computing system, such as the one illustrated in FIG. 27. The example computer system 2702 is in communication with one or more computing systems 2720, portable devices 2715, and/or one or more data sources 2722 via one or more networks 2718. While FIG. 27 illustrates an embodiment of a computing system 2702, it is recognized that the functionality provided for in the components and modules of computer system 2702 may be combined into fewer components and modules, or further separated into additional components and modules.

The computer system 2702 can comprise a module 2714 that carries out the functions, methods, acts, and/or processes described herein (e.g., processes as discussed above). The module 2714 is executed on the computer system 2702 by a central processing unit 2706 discussed further below.

In general, the word "module," as used herein, refers to logic embodied in hardware or firmware or to a collection of software instructions, having entry and exit points. Modules are written in a program language, such as JAVA, C or C++, Python, or the like. Software modules may be compiled or linked into an executable program, installed in a dynamic link library, or may be written in an interpreted language such as BASIC, PERL, LUA, or Python. Software modules may be called from other modules or from themselves, and/or may be invoked in response to detected events or interruptions. Modules implemented in hardware include connected logic units such as gates and flip-flops, and/or may include programmable units, such as programmable gate arrays or processors.

Generally, the modules described herein refer to logical modules that may be combined with other modules or divided into sub-modules despite their physical organization or storage. The modules are executed by one or more computing systems and may be stored on or within any suitable computer readable medium or implemented in-whole or in-part within special designed hardware or firmware. Not all calculations, analysis, and/or optimization require the use of computer systems, though any of the above-described methods, calculations, processes, or analyses may be facilitated through the use of computers. Further, in some embodiments, process blocks described herein may be altered, rearranged, combined, and/or omitted.

The computer system 2702 includes one or more processing units (CPU) 2706, which may comprise a microprocessor. The computer system 2702 further includes a physical memory 2710, such as random-access memory (RAM) for temporary storage of information, a read only memory (ROM) for permanent storage of information, and a mass storage device 2704, such as a backing store, hard drive, rotating magnetic disks, solid state disks (SSD), flash memory, phase-change memory (PCM), 27D XPoint memory, diskette, or optical media storage device. Alternatively, the mass storage device may be implemented in an array of servers. Typically, the components of the computer system 2702 are connected to the computer using a standards-based bus system. The bus system can be implemented using various protocols, such as Peripheral Component Interconnect (PCI), Micro Channel, SCSI, Industrial Standard Architecture (ISA) and Extended ISA (EISA) architectures.

The computer system 2702 includes one or more input/output (I/O) devices and interfaces 2712, such as a keyboard, mouse, touch pad, and printer. The I/O devices and interfaces 2712 can include one or more display devices, such as a monitor, that allows the visual presentation of data to a user. More particularly, a display device provides for the presentation of GUIs as application software data, and multi-media presentations, for example. The I/O devices and interfaces 2712 can also provide a communications interface to various external devices. The computer system 2702 may comprise one or more multi-media devices 2708, such as speakers, video cards, graphics accelerators, and microphones, for example.

The computer system 2702 may run on a variety of computing devices, such as a server, a Windows server, a Structure Query Language server, a Unix Server, a personal computer, a laptop computer, and so forth. In other embodiments, the computer system 2702 may run on a cluster computer system, a mainframe computer system and/or other computing system suitable for controlling and/or communicating with large databases, performing high volume transaction processing, and generating reports from large databases. The computing system 2702 is generally controlled and coordinated by an operating system software, such as z/OS, Windows, Linux, UNIX, BSD, SunOS, Solaris, macOS, iOS, iPadOS, Android, or other compatible operating systems, including proprietary operating systems. Operating systems control and schedule computer processes for execution, perform memory management, provide file system, networking, and I/O services, and provide a user interface, such as a graphical user interface (GUI), among other things.

The computer system 2702 illustrated in FIG. 27 is coupled to a network 2718, such as a LAN, WAN, or the Internet via a communication link 2716 (wired, wireless, or a combination thereof). Network 2718 communicates with various computing devices and/or other electronic devices. Network 2718 is communicating with one or more computing systems 2720, one or more portable devices 2715 and one or more data sources 2722. The module 2714 may access or may be accessed by computing systems 2720, portable devices 2715 and/or data sources 2722 through a web-enabled user access point. Connections may be a direct physical connection, a virtual connection, and other connection type. The web-enabled user access point may comprise a browser module that uses text, graphics, audio, video, and other media to present data and to allow interaction with data via the network 2718.

Access to the module 2714 of the computer system 2702 by computing systems 2720, portable devices 2715, and/or by data sources 2722 may be through a web-enabled user access point such as the computing systems' 2720 or data source's 2722 personal computer, cellular phone, smartphone, laptop, tablet computer, e-reader device, audio player, or another device capable of connecting to the network 2718. Such a device may have a browser module that is implemented as a module that uses text, graphics, audio, video, and other media to present data and to allow interaction with data via the network 2718.

The output module may be implemented as a combination of an all-points addressable display such as a cathode ray tube (CRT), a liquid crystal display (LCD), a plasma display, or other types and/or combinations of displays. The output module may be implemented to communicate with input devices 2712 and they also include software with the appropriate interfaces which allow a user to access data through the use of stylized screen elements, such as menus, windows, dialogue boxes, tool bars, and controls (for example, radio buttons, check boxes, sliding scales, and so forth). Furthermore, the output module may communicate with a set of input and output devices to receive signals from the user.

The input device(s) may comprise a keyboard, roller ball, pen and stylus, mouse, trackball, voice recognition system, or pre-designated switches or buttons. The output device(s) may comprise a speaker, a display screen, a printer, or a voice synthesizer. In addition, a touch screen may act as a hybrid input/output device. In another embodiment, a user may interact with the system more directly such as through a system terminal connected to the score generator without communications over the Internet, a WAN, or LAN, or similar network.

In some embodiments, the system 2702 may comprise a physical or logical connection established between a remote microprocessor and a mainframe host computer for the express purpose of uploading, downloading, or viewing interactive data and databases online in real time. The remote microprocessor may be operated by an entity operating the computer system 2702, including the client server systems or the main server system, and/or may be operated by one or more of the data sources 2722, one or more of the portable devices 2715 and/or one or more of the computing systems 2720. In some embodiments, terminal emulation software may be used on the microprocessor for participating in the micro-mainframe link.

In some embodiments, computing systems 2720 who are internal to an entity operating the computer system 2702 may access the module 2714 internally as an application or process run by the CPU 2706.

In some embodiments, one or more features of the systems, methods, and devices described herein can utilize a URL and/or cookies, for example for storing and/or transmitting data or user information. A Uniform Resource Locator (URL) can include a web address and/or a reference to a web resource that is stored on a database and/or a server. The URL can specify the location of the resource on a computer and/or a computer network. The URL can include a mechanism to retrieve the network resource. The source of the network resource can receive a URL, identify the location of the web resource, and transmit the web resource back to the requestor. A URL can be converted to an IP address, and a Domain Name System (DNS) can look up the URL and its corresponding IP address. URLs can be references to web pages, file transfers, emails, database accesses, and other applications. The URLs can include a sequence of characters that identify a path, domain name, a file extension, a host name, a query, a fragment, scheme, a protocol identifier, a port number, a username, a password, a flag, an object, a resource name and/or the like. The systems disclosed herein can generate, receive, transmit, apply, parse, serialize, render, and/or perform an action on a URL.

A cookie, also referred to as an HTTP cookie, a web cookie, an internet cookie, and a browser cookie, can include data sent from a website and/or stored on a user's computer. This data can be stored by a user's web browser while the user is browsing. The cookies can include useful information for websites to remember prior browsing information, such as a shopping cart on an online store, clicking of buttons, login information, and/or records of web pages or network resources visited in the past. Cookies can also include information that the user enters, such as names, addresses, passwords, credit card information, etc. Cookies can also perform computer functions. For example, authentication cookies can be used by applications (for example, a web browser) to identify whether the user is already logged in (for example, to a web site). The cookie data can be encrypted to provide security for the consumer. Tracking cookies can be used to compile historical browsing histories of individuals. Systems disclosed herein can generate and use cookies to access data of an individual. Systems can also generate and use JSON web tokens to store authenticity information, HTTP authentication as authentication protocols, IP addresses to track session or identity information, URLs, and the like.

The computing system 2702 may include one or more internal and/or external data sources (for example, data sources 2722). In some embodiments, one or more of the data repositories and the data sources described above may be implemented using a relational database, such as DB2, Sybase, Oracle, CodeBase, and Microsoft® SQL Server as well as other types of databases such as a flat-file database, an entity relationship database, and object-oriented database, and/or a record-based database.

The computer system 2702 may also access one or more databases 2722. The databases 2722 may be stored in a database or data repository. The computer system 2702 may access the one or more databases 2722 through a network 2718 or may directly access the database or data repository through I/O devices and interfaces 2712. The data repository storing the one or more databases 2722 may reside within the computer system 2702.

ADDITIONAL EMBODIMENTS

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than restrictive sense.

Indeed, although this invention has been disclosed in the context of certain embodiments and examples, it will be understood by those skilled in the art that the invention extends beyond the specifically disclosed embodiments to other alternative embodiments and/or uses of the invention and obvious modifications and equivalents thereof. In addition, while several variations of the embodiments of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes of the embodiments of the disclosed invention. Any methods disclosed herein need not be performed in the order recited. Thus, it is intended that the scope of the invention herein disclosed should not be limited by the particular embodiments described above.

It will be appreciated that the systems and methods of the disclosure each have several innovative aspects, no single one of which is solely responsible or required for the desirable attributes disclosed herein. The various features and processes described above may be used independently of one another or may be combined in various ways. All possible combinations and subcombinations are intended to fall within the scope of this disclosure.

Certain features that are described in this specification in the context of separate embodiments also may be implemented in combination in a single embodiment. Conversely, various features that are described in the context of a single embodiment also may be implemented in multiple embodiments separately or in any suitable subcombination. Moreover, although features may be described above as acting in certain combinations and even initially claimed as such, one or more features from a claimed combination may in some cases be excised from the combination, and the claimed combination may be directed to a subcombination or variation of a subcombination. No single feature or group of features is necessary or indispensable to each and every embodiment.

It will also be appreciated that conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. In addition, the term "or" is used in its inclusive sense (and not in its exclusive sense) so that when used, for example, to connect a list of elements, the term "or" means one, some, or all of the elements in the list. In addition, the articles "a," "an," and "the" as used in this application and the appended claims are to be construed to mean "one or more" or "at least one" unless specified otherwise. Similarly, while operations may be depicted in the drawings in a particular order, it is to be recognized that such operations need not be performed in the particular order shown or in sequential order, or that all illustrated operations be performed, to achieve desirable results. Further, the drawings may schematically depict one or more example processes in the form of a flowchart. However, other operations that are not depicted may be incorporated in the example methods and processes that are schematically illustrated. For example, one or more additional operations may be performed before, after, simultaneously, or between any of the illustrated operations. Additionally, the operations may be rearranged or reordered in other embodiments. In certain circumstances, multitasking and parallel processing may be advantageous. Moreover, the separation of various system components in the embodiments described above should not be understood as requiring such separation in all embodiments, and it should be understood that the described program components and systems may generally be integrated together in a single software product or packaged into multiple software products. Additionally, other embodiments are within the scope of the following claims. In some cases, the actions recited in the claims may be performed in a different order and still achieve desirable results.

Further, while the methods and devices described herein may be susceptible to various modifications and alternative forms, specific examples thereof have been shown in the drawings and are herein described in detail. It should be understood, however, that the invention is not to be limited to the particular forms or methods disclosed, but, to the contrary, the invention is to cover all modifications, equivalents, and alternatives falling within the spirit and scope of the various implementations described and the appended claims. Further, the disclosure herein of any particular feature, aspect, method, property, characteristic, quality, attribute, element, or the like in connection with an implementation or embodiment can be used in all other implementations or embodiments set forth herein. Any methods disclosed herein need not be performed in the order recited. The methods disclosed herein may include certain actions taken by a practitioner; however, the methods can also include any third-party instruction of those actions, either expressly or by implication. The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 8.5 mm" includes "3.5 mm." Phrases preceded by a term such as "substantially" include the recited phrase and should be interpreted based on the circumstances (e.g., as much as reasonably possible under the circumstances). For example, "substantially constant" includes "constant." Unless stated otherwise, all measurements are at standard conditions including temperature and pressure.

As used herein, a phrase referring to "at least one of" a list of items refers to any combination of those items, including single members. As an example, "at least one of: A, B, or C" is intended to cover: A, B, C, A and B, A and C, B and C, and A, B, and C. Conjunctive language such as the phrase "at least one of X, Y and Z," unless specifically stated otherwise, is otherwise understood with the context as used in general to convey that an item, term, etc. may be at least one of X, Y or Z. Thus, such conjunctive language is not generally intended to imply that certain embodiments require at least one of X, at least one of Y, and at least one of Z to each be present. The headings provided herein, if any, are for convenience only and do not necessarily affect the scope or meaning of the devices and methods disclosed herein.

Accordingly, the claims are not intended to be limited to the embodiments shown herein, but are to be accorded the widest scope consistent with this disclosure, the principles and the novel features disclosed herein.

What is claimed is:

1. A computer system for generating a model for electronically generating a digitally stained medical image of a tissue sample, the computer system comprising:
   a camera;
   one or more processors; and
   an electronic storage medium,
   the camera configured to receive first visible light through an aperture of the camera;
   the camera configured to generate a first image comprising red, green, and blue channels from the received first visible light, wherein the first image is a first RGB image of an unstained tissue sample;
   the camera configured to receive second visible light through the aperture of the camera;
   the camera configured to generate a second image comprising red, green, and blue channels from the received second visible light, wherein the second image is a second RGB image of a stained tissue sample,
   wherein the unstained tissue sample and the stained tissue comprise a same tissue;
   the camera is in electronic communication with the one or more processors and the electronic storage medium;
   the camera configured to electronically store the first and second images in the electronic storage medium;
   the electronic storage medium comprises instructions that, when executed by the one or more processors, cause the one or more processors to:
      execute first registration instructions comprising:
         determining a first difference between the first image and the second image;
         modifying one or more of the first image and the second image, wherein the modifying comprises one or more of rotation, translation, or deformation;
         determining a second difference between first image and the second image;
         determining that the second difference between the first image and second image is within an acceptable threshold value; and
         generating a co-registered image pair comprising an unstained image and a ground truth image, wherein the unstained image comprises the first image or the modified first image and the ground truth image comprises the second image or the modified second image;
      execute a first model training process comprising:
         digitally staining the unstained image to generate a first digitally stained image; and
         computing a loss function, wherein the loss function considers a subset of ground truth image data and a subset of digitally stained image data considers the differences between individual pixels of the ground truth image and the first digitally stained image and differences in a spatial distribution of colors in the ground truth image and the first digitally stained image; and
         based at least in part on a result of the loss function, adjusting one or more weights of the model;
         determining that an output of the loss function is within a threshold amount;
      execute second registration instructions comprising:
         determining a third difference between the first digitally stained image generated by the trained model and the ground truth image;
         modifying one or more of the unstained image and the ground truth image, wherein the modifying comprises one or more of rotation, translation, or deformation;
         determining a fourth difference between the first digitally stained image and the ground truth image;
         determining that the fourth difference is less within another acceptable threshold value; and
         generating a second co-registered image pair comprising a second ground truth image comprising the ground truth image or the modified ground truth image and a second unstained image comprising the unstained image or the modified unstained image;
      execute a second model training process comprising:
         digitally staining the second unstained image to generate a second digitally stained image;
         computing a second loss function, wherein the second loss function considers a subset of second ground truth image data and a subset of second digitally stained image data; and
         based on a result of the second loss function, adjusting one or more weights of the model; and
      store a generated digital staining model generated by the first model training process and the second model training process in the electronic storage medium, wherein the generated digital staining model comprises the one or more weights.

2. The system of claim 1, wherein the camera comprises a Bayer filter and one of a charge-coupled device sensor or a complementary metal oxide semiconductor sensor.

3. The system of claim 1, wherein the first registration instructions further comprise:
   denoising at least one of the first image or the second image.

4. The system of claim 1, wherein a difference between a first structural similarity index for the co-registered image pair and a second structural similarity index measure for the second co-registered image pair is about eight percent.

5. The system of claim 1, wherein digitally staining the unstained image comprises:
   dividing the unstained image into a first plurality of subfields, each subfield of the first plurality of subfields representing a subset of the unstained image;

dividing the stained image into a second plurality of subfields, each subfield of the second plurality of subfields representing a subset of the stained image, wherein each subfield of the second plurality of subfields corresponds to a subfield of the first plurality of subfields;

digitally staining each subfield of the second plurality of subfields; and combining each digitally stained subfield to form the digitally stained image.

6. The system of claim 5, wherein at least one subfield of the plurality overlaps with another field of the plurality of subfields.

7. The system of claim 5, wherein a size of a subfield is at least 256 pixels by 256 pixels.

8. The system of claim 7, wherein the size of a subfield is 512 pixels by 512 pixels.

9. A method for generating a model for electronically generating a digitally stained medical image of a tissue sample, the method comprising:

receiving a first image comprising red, green, and blue channels, wherein the first image is an image of an unstained tissue sample, wherein the first image was captured using a camera;

receiving a second image comprising red, green, and blue channels, wherein the second image is an image of a stained tissue sample, wherein the second image was captured using the camera, wherein the unstained tissue sample and the stained tissue comprise a same tissue;

execute first registration instructions comprising:
  determining a first difference between the first image and the second image;
  modifying one or more of the first image and the second image, wherein the modifying comprises one or more of rotation, translation, or deformation;
  determining a second difference between first image and the second image;
  determining that the second difference between the first image and second image is within an acceptable threshold value; and
  generating a co-registered image pair comprising an unstained image and a ground truth image, wherein the unstained image comprises the first image or the modified first image and the ground truth image comprises the second image or the modified second image;

execute a first model training process comprising:
  digitally staining the unstained image to generate a first digitally stained image; and
  computing a loss function, wherein the loss function considers a subset of ground truth image data and a subset of digitally stained image data considers the differences between individual pixels of the ground truth image and the first digitally stained image and differences in a spatial distribution of colors in the ground truth image and the first digitally stained image; and
  based at least in part on a result of the loss function, adjusting one or more weights of the model;
  determining that an output of the loss function is within a threshold amount;

execute second registration instructions comprising:
  determining a third difference between the a digitally stained image generated by the trained model and the ground truth image;
  modifying one or more of the unstained image and the ground truth image, wherein the modifying comprises one or more of rotation, translation, or deformation;
  determining a fourth difference between the first digitally stained image and the ground truth image;
  determining that the fourth difference is less within another acceptable threshold value; and
  generating a second co-registered image pair comprising a second ground truth image comprising the ground truth image or the modified ground truth image and a second unstained image comprising the unstained image or the modified unstained image;

execute a second model training process comprising:
  digitally staining the second unstained image to generate a second digitally stained image;
  computing a second loss function, wherein the second loss function considers a subset of second ground truth image data and a subset of second digitally stained image data; and
  based on a result of the second loss function, adjusting one or more weights of the model; and store a generated digital staining model generated by the first model training process and the second model training process in an electronic storage medium, wherein the generated digital staining model comprises the one or more weights.

10. The method of claim 9, wherein the method is repeated using a second tissue sample from a second donor that is different from a first donor of the tissue sample.

11. The method of claim 9, wherein a registration error between the unstained image and the ground truth image is less than about 10 pixels, wherein the registration error is a measure of an offset between the unstained image and the ground truth image.

12. The method of claim 9, wherein the first registration instructions further comprise:
  denoising at least one of the first image or the second image.

13. The method of claim 9, wherein a registration error between the first image and the second image is less than about 10 pixels, wherein the registration error is a measure of an offset between the first image and second image.

14. The method of claim 9, wherein digitally staining the unstained image comprises:
  dividing the unstained image into a first plurality of subfields, each subfield of the first plurality of subfields representing a subset of the unstained image;
  diving the stained image into a second plurality of subfields, each subfield of the second plurality of subfields representing a subset of the stained image, wherein each subfield of the second plurality of subfields corresponds to a subfield of the first plurality of subfields;
  digitally staining each subfield of the second plurality of subfields; and
  combining each digitally stained subfield to form the digitally stained image.

15. The method of claim 14, wherein at least one subfield of the plurality overlaps with another field of the plurality of subfields.

16. The method of claim 14, wherein a size of a subfield is at least 256 pixels by 256 pixels.

17. The method of claim 16, wherein the size of a subfield is 512 pixels by 512 pixels.

18. A system for electronically generating a digitally stained medical image of a tissue sample, the system comprising:
- a camera;
- one or more processors; and
- an electronic storage medium,
- the camera configured to receive visible light through an aperture of the camera;
- the camera configured to generate an unstained image comprising red, green, and blue channels from the received visible light, wherein the unstained image is an image of the tissue sample;
- the camera configured to be in electronic communication with the one or more processors and the electronic storage medium and to store the unstained image in the electronic storage medium;
- the electronic storage medium comprising instructions that, when executed by the one or more processors cause the system to:
  - preprocess the unstained image;
  - provide the preprocessed unstained image to a generated model, wherein the generated model is trained according to claim 9;
  - generate, by the generated model using the preprocessed image, a digitally stained image; and
  - normalize colors of the digitally stained image.

19. The system of claim 18, wherein normalizing the colors of the digitally stained images comprises:
- converting a reference image to a first YCbCr image, wherein the first YCbCr image comprises a luma component (Y), a blue-difference chroma component (Cb), and a red-difference chroma component (Cr);
- determining a mean value for each of the luma component, the blue-difference chroma component, and the red-difference chroma component of the first YCbCr image;
- determining a standard deviation value for each of the luma component, the blue-difference chroma component, and the red-difference chroma component of the first YCbCr image;
- converting to digitally stained image to a second YCbCr image, wherein the second YCbCr image comprises a luma component (Y), a blue-difference chroma component (Cb), and a read-difference chroma component (Cr);
- determining a mean value for each of the luma component, the blue-difference chroma component, and the red-difference chroma component of the second YCbCr image;
- determining a standard deviation value for each of the luma component, the blue-difference chroma component, and the red-difference chroma component of the second YCbCr image;
- for each pixel of the second YCbCr image, determining a standard deviation of the luma component, the blue-difference chroma component, and the red-difference chroma component;
- for each pixel in the second YCbCr image:
  - determining a difference between the luma component value of the pixel and the mean value of the luma component for the second YCbCr image;
  - modifying the value of the luma component of the pixel based on the determined difference, the mean luma value of the first YCbCr image, and the standard deviation of the luma value of the first YCbCr image;
  - determining a difference between the blue-difference chroma component value of the pixel and the mean value of the blue-difference chroma component of the second YCbCr image;
  - modifying the value of the blue-difference chroma component of the pixel based on the determined difference, the mean blue difference chroma component value of the first YCbCr image, and the standard deviation of the blue difference chroma component value of the first YCbCr image;
  - determining a difference between the red-difference component value of the pixel and the mean value of the red-difference chroma component of the second YCbCr image;
  - modifying the value of the red-difference chroma component of the pixel based on the determined difference, the mean red-difference chroma component value of the first YCbCr image, and the standard deviation of the red-difference chroma component value of the first YCbCr image;
  - converting the modified values to red, green, and blue values; and
  - generating an RGB image using the red, green, and blue values.

20. The system of claim 19, wherein the reference image is an image of a same tissue type as the tissue sample.

* * * * *